US009693928B2

(12) United States Patent
Martin et al.

(10) Patent No.: US 9,693,928 B2
(45) Date of Patent: Jul. 4, 2017

(54) SWALLOWING AIR PULSE THERAPY MOUTHPIECE AND METHOD FOR THE USE THEREOF

(71) Applicants: Ruth E. Martin, London (CA); Michael Nuttall, London (CA); Michael A. Baran, London (CA); George Baran, London (CA); Bryan Finlay, London (CA); Julie Theurer, London (CA); Sarah Trotter, Bailieboro (CA)

(72) Inventors: Ruth E. Martin, London (CA); Michael Nuttall, London (CA); Michael A. Baran, London (CA); George Baran, London (CA); Bryan Finlay, London (CA); Julie Theurer, London (CA); Sarah Trotter, Bailieboro (CA)

(73) Assignees: Trudell Medical International, London (CA); The University of Western Ontario, London (CA)

( * ) Notice: Subject to any disclaimer, the term of this patent is extended or adjusted under 35 U.S.C. 154(b) by 619 days.

(21) Appl. No.: 14/013,470

(22) Filed: Aug. 29, 2013

(65) Prior Publication Data
US 2014/0194792 A1 Jul. 10, 2014

Related U.S. Application Data

(63) Continuation of application No. 12/424,191, filed on Apr. 15, 2009, now Pat. No. 8,540,660.
(Continued)

(51) Int. Cl.
*A61H 13/00* (2006.01)
*A61H 9/00* (2006.01)
(Continued)

(52) U.S. Cl.
CPC .............. *A61H 13/00* (2013.01); *A61H 9/00* (2013.01); *A61H 9/005* (2013.01); *A61H 13/005* (2013.01);
(Continued)

(58) Field of Classification Search
CPC ..................... A61M 16/0488–16/0497; A61M 16/00–16/0003;
(Continued)

(56) References Cited

U.S. PATENT DOCUMENTS 683,075 A    9/1901  Schneider
2,672,143 A * 3/1954  Gold .................. A61C 17/0211
                                                  433/80
(Continued)

FOREIGN PATENT DOCUMENTS

CA    2064882 A1    2/1991
CA    2203257 A1    5/1996
(Continued)

OTHER PUBLICATIONS

Office Action in U.S. Appl. No. 11/411,241, dated Nov. 13, 2009, 12 pgs.
(Continued)

*Primary Examiner* — Justine Yu
*Assistant Examiner* — Colin W Stuart
(74) *Attorney, Agent, or Firm* — Brinks Gilson & Lione

(57) ABSTRACT

An oral appliance for administering a stimulus, such as a substance, to the mouth of a user includes a flexible tube having an inlet portion, a first curved portion forming an ear loop connected to the inlet portion, a second curved portion forming a lip bend connected to the first curved portion, and an outlet portion extending from the second curved portion. Alternatively, a mouthpiece for delivering a substance to the mouth of a user includes a housing having an inlet portion,
(Continued)

a riser portion extending upwardly from the inlet portion and a curved outlet portion. A flexible tube is coupled to the housing. A method of delivering a substance to a predetermined location in a user's mouth includes disposing a flexible tube between a row of teeth and an interior surface of a cheek. The flexible tube has an exit port positioned in a rear portion of the user's mouth. No portion of the flexible tube is disposed between the upper and lower teeth of the user such that the upper and lower teeth can be closed against each other. The method further includes dispensing a substance through the exit port.

18 Claims, 14 Drawing Sheets

Related U.S. Application Data

(60) Provisional application No. 61/071,144, filed on Apr. 15, 2008.

(51) Int. Cl.
*A61H 21/00* (2006.01)
*A61M 11/00* (2006.01)
*A61M 16/06* (2006.01)
*A61N 1/05* (2006.01)
*A61N 1/36* (2006.01)

(52) U.S. Cl.
CPC ............ *A61H 21/00* (2013.01); *A61M 11/00* (2013.01); *A61M 16/0666* (2013.01); *A61M 2202/025* (2013.01); *A61M 2202/0208* (2013.01); *A61M 2210/0625* (2013.01); *A61N 1/0548* (2013.01); *A61N 1/36007* (2013.01)

(58) Field of Classification Search
CPC .............. A61M 16/0057–16/0084; A61M 16/0096–16/01; A61M 16/06; A61M 16/10; A61M 16/104; A61M 16/1045; A61M 16/12–16/14; A61M 16/16; A61M 16/18; A61H 9/00; A61H 9/005; A61H 13/00; A61H 13/005; A61C 17/00; A61C 17/02; A61C 17/0211; A61C 17/022; A61C 17/028
USPC ........ 128/848, 859, 861, 862; 601/154, 162, 601/164, 165
See application file for complete search history.

(56) References Cited

U.S. PATENT DOCUMENTS

| | | | |
|---|---|---|---|
| 2,957,476 A | 10/1960 | Freeman | |
| 3,731,675 A | 5/1973 | Kelly | |
| 3,799,170 A * | 3/1974 | Walsh | A61M 29/02 601/160 |
| 3,853,105 A | 12/1974 | Kenagy | |
| 4,071,026 A | 1/1978 | Bevins | |
| 4,164,940 A * | 8/1979 | Quinby | A61H 13/00 433/216 |
| 4,170,230 A | 10/1979 | Nelson | |
| 4,560,351 A * | 12/1985 | Osborne | A61C 19/08 433/215 |
| 4,572,177 A | 2/1986 | Tiep et al. | |
| 4,576,190 A | 3/1986 | Youssef | |
| 4,676,774 A | 6/1987 | Semm et al. | |
| 4,679,551 A | 7/1987 | Anthony | |
| 4,773,898 A | 9/1988 | Begouen | |
| 4,790,305 A | 12/1988 | Zoltan et al. | |
| 4,966,580 A * | 10/1990 | Turner | A61J 15/0011 215/11.4 |
| 4,996,990 A | 3/1991 | Hideshima | |
| 5,066,502 A | 11/1991 | Eales | |
| 5,085,634 A | 2/1992 | Lackney | |
| 5,143,087 A | 9/1992 | Yarkony | |
| 5,147,298 A | 9/1992 | Turner et al. | |
| 5,176,151 A | 1/1993 | Harding | |
| 5,213,553 A | 5/1993 | Light | |
| 5,365,624 A * | 11/1994 | Berns | A61C 17/0211 15/22.1 |
| 5,377,688 A | 1/1995 | Aviv et al. | |
| 5,503,629 A | 4/1996 | Catone et al. | |
| 5,515,860 A | 5/1996 | Aviv et al. | |
| H1557 H | 7/1996 | Joubert et al. | |
| 5,566,645 A | 10/1996 | Cole | |
| 5,725,564 A | 3/1998 | Freed et al. | |
| 5,735,772 A | 4/1998 | Schiavoni | |
| 5,826,570 A | 10/1998 | Goodman et al. | |
| 5,855,908 A | 1/1999 | Stanley et al. | |
| 5,884,625 A | 3/1999 | Hart | |
| 5,891,185 A | 4/1999 | Freed et al. | |
| 5,897,492 A | 4/1999 | Feller et al. | |
| 5,950,624 A | 9/1999 | Hart | |
| 5,954,673 A | 9/1999 | Staehlin et al. | |
| 5,970,978 A | 10/1999 | Aviv et al. | |
| 5,993,413 A | 11/1999 | Aaltonen et al. | |
| 6,036,655 A | 3/2000 | Aviv et al. | |
| D422,694 S | 4/2000 | Hill | |
| 6,104,958 A | 8/2000 | Freed et al. | |
| 6,264,058 B1 | 7/2001 | Porter et al. | |
| 6,295,988 B1 | 10/2001 | Sue | |
| 6,299,592 B1 | 10/2001 | Zander | |
| 6,355,003 B1 | 3/2002 | Aviv et al. | |
| 6,454,788 B1 | 9/2002 | Ashton | |
| 6,484,053 B2 | 11/2002 | Leelamanit | |
| 6,591,140 B2 | 7/2003 | Strome et al. | |
| 6,607,549 B2 | 8/2003 | Huang | |
| 6,689,078 B1 * | 2/2004 | Rehkemper | A61C 17/30 15/29 |
| 6,729,942 B2 * | 5/2004 | Harris | A61C 3/025 433/125 |
| 6,805,127 B1 | 10/2004 | Karasic | |
| 6,893,259 B1 | 5/2005 | Reizenson | |
| 6,916,287 B2 | 7/2005 | Dematteis et al. | |
| 6,935,857 B1 | 8/2005 | Farrell | |
| 6,960,183 B2 | 11/2005 | Nicolette | |
| 7,021,930 B2 | 4/2006 | Schemmer et al. | |
| 7,039,468 B2 | 5/2006 | Freed et al. | |
| 7,083,548 B1 | 8/2006 | Moore et al. | |
| 7,118,377 B2 | 10/2006 | Inoue et al. | |
| 7,147,468 B2 | 12/2006 | Snyder et al. | |
| 7,238,145 B2 | 7/2007 | Robbins et al. | |
| 7,239,918 B2 | 7/2007 | Strother et al. | |
| 7,273,327 B2 | 9/2007 | Hohlbein et al. | |
| 7,477,947 B2 | 1/2009 | Pines et al. | |
| 7,660,636 B2 | 2/2010 | Castel et al. | |
| 2002/0082544 A1 | 6/2002 | Thrash et al. | |
| 2003/0015198 A1 | 1/2003 | Heeke et al. | |
| 2003/0104342 A1 | 6/2003 | Lynch et al. | |
| 2004/0000054 A1 | 1/2004 | Sommer | |
| 2004/0072122 A1 * | 4/2004 | Hegemann | A61C 1/0092 433/80 |
| 2004/0138585 A1 | 7/2004 | Dematteis et al. | |
| 2005/0103331 A1 | 5/2005 | Wedemeyer | |
| 2005/0222535 A1 | 10/2005 | Uesugi et al. | |
| 2006/0110710 A1 | 5/2006 | Schemmer et al. | |
| 2006/0210480 A1 | 9/2006 | Hamdy | |
| 2006/0235352 A1 | 10/2006 | Dziewas et al. | |
| 2006/0282010 A1 | 12/2006 | Martin et al. | |
| 2007/0156182 A1 | 7/2007 | Castel et al. | |
| 2008/0009810 A1 | 1/2008 | Hamdy | |
| 2008/0077192 A1 | 3/2008 | Harry et al. | |
| 2008/0147142 A1 | 6/2008 | Testerman et al. | |
| 2008/0251597 A1 | 10/2008 | Pearson | |
| 2008/0269837 A1 | 10/2008 | Ludlow et al. | |
| 2008/0269856 A1 | 10/2008 | Cross et al. | |
| 2008/0269857 A1 | 10/2008 | Cross et al. | |
| 2008/0269858 A1 | 10/2008 | Cross et al. | |
| 2008/0269859 A1 | 10/2008 | Cross et al. | |
| 2008/0269860 A1 | 10/2008 | Cross et al. | |

(56) References Cited

U.S. PATENT DOCUMENTS

| | | |
|---|---|---|
| 2008/0269861 A1 | 10/2008 | Cross et al. |
| 2009/0018611 A1 | 1/2009 | Campbell et al. |
| 2009/0048645 A1 | 2/2009 | Philipp et al. |
| 2009/0048647 A1 | 2/2009 | Tingey |
| 2009/0054980 A1 | 2/2009 | Ludlow et al. |
| 2009/0120446 A1 | 5/2009 | Vaska et al. |
| 2009/0120447 A1 | 5/2009 | Vaska et al. |
| 2009/0123886 A1 | 5/2009 | Vaska |
| 2009/0137859 A1 | 5/2009 | Belafsky et al. |
| 2009/0249571 A1 | 10/2009 | Rohrig |
| 2009/0259310 A1 | 10/2009 | Blom |
| 2009/0286237 A1 | 11/2009 | Fitzgerald et al. |
| 2009/0306626 A1 | 12/2009 | Sinha et al. |
| 2009/0306741 A1 | 12/2009 | Hogle et al. |
| 2010/0010400 A1 | 1/2010 | Martin et al. |
| 2010/0055233 A1 | 3/2010 | Macinnis et al. |
| 2010/0121224 A1 | 5/2010 | Toyota et al. |

FOREIGN PATENT DOCUMENTS

| | | |
|---|---|---|
| EP | 1 314 430 B1 | 9/2007 |
| JP | 11309186 A | 11/1999 |
| WO | WO 90/10470 A1 | 9/1990 |
| WO | WO 02/38012 A2 | 5/2002 |
| WO | WO 03/061453 A2 | 7/2003 |
| WO | WO 2004/028433 A2 | 4/2004 |
| WO | WO 2004/028433 A3 | 4/2004 |
| WO | WO 2004/069076 A2 | 8/2004 |
| WO | WO 2004/075743 A1 | 9/2004 |
| WO | WO 2005/070316 A1 | 8/2005 |
| WO | WO 2005/102458 A2 | 11/2005 |
| WO | WO 2005/122877 A1 | 12/2005 |
| WO | WO 2006/024825 A1 | 3/2006 |
| WO | WO 2006/083217 A1 | 8/2006 |
| WO | WO 2006/106327 A1 | 10/2006 |
| WO | WO 2006/108066 A2 | 10/2006 |
| WO | WO 2006/116843 A1 | 11/2006 |
| WO | WO 2006/108066 A3 | 12/2006 |
| WO | WO 2007/005582 A1 | 1/2007 |
| WO | WO 2007/021468 A2 | 2/2007 |
| WO | WO 2007/021468 A3 | 2/2007 |
| WO | WO 2007/022034 A2 | 2/2007 |
| WO | WO 2007/081764 A2 | 7/2007 |
| WO | WO 2007/081764 A3 | 7/2007 |
| WO | WO 2007/123746 A2 | 11/2007 |
| WO | WO 2007/123746 A3 | 11/2007 |
| WO | WO 2008/076646 A1 | 6/2008 |
| WO | WO 2009/127947 A2 | 10/2009 |

OTHER PUBLICATIONS

Office Action in Chinese Application No. 200680014928.9, dated Mar. 6, 2009, 5 pgs.

Office Action in Chinese Application No. 200680014928.9, dated Nov. 27, 2009, 6 pgs.

International Search Report in PCT Application No. PCT/CA2006/000650, dated Sep. 6, 2006, 2 pgs.

International Search Report in PCT Application No. PCT/IB 2009/005252, dated Oct. 7, 2006, 5 pgs.

Supplementary EPO Search Report in EP Application No. 06721849.5, dated Nov. 24, 2009, 11 pgs.

Office Action from Japanese Application No. 2011-504588, dated Jun. 4, 2013, 4 pages (with English translation).

Ali, Galib N. et al., "Influence of Cold Stimulation on the Normal Pharyngeal Swallow Response", Dysphagia, 1996, vol. 11, pp. 2-8.

Aviv, Jonathan E. et al., "Air Pulse Quantification of Supraglottic and Pharyngeal Sensation: A New Technique", Ann Otol Rhinol Laryngol, 1993, vol. 102, pp. 777-780.

Aviv, Jonathan E. et al., "Clinical assessment of Pharyngolaryngeal Sensitivity", The American Journal of Medicine, 2000, vol. 108 (4A), pp. 68S-72S.

Aviv, Jonathan E. et al., "Effects of Aging on Sensitivity of the Pharyngeal and Supraglottic Areas", The American Journal of Medicine, 1997, vol. 103 (5A), pp. 74S-76S.

Aviv, Jonathan E. et al., "Laryngopharyngeal Sensory Deficts in Patients with Laryngopharyngeal Reflux and Dysohagia", Ann Otol Rhinol Laryngol, 2000, vol. 109, pp. 1000-1006.

Aviv, Jonathan E. et al., "Laryngopharyngeal Sensory Discrimination Testing and the Laryngeal Adductor Reflex", Ann Otol Rhinol Laryngol, 1999, vol. 108, pp. 725-730.

Aviv, Jonathan E. et al., "Silent Laryngopharyngeal Sensory Deficits After Stroke", Ann Otol Rhinol Laryngol, 1997, vol. 106, pp. 87-93.

Aviv, Jonathan E. et al., "Supraglottic and Pharyngeal sensory Abnormalities in Stroke patients with Dysphagia", Ann Otol Rhinol Laryngol, 1996, vol. 105, pp. 92-97.

Aviv, Jonathan E. et al., "Surface sensibility of the floor of the mouth and tongue in healthy controls and in radiated patients", Annual Meeting of the American Academy of Otolaryngology—Head and Neck Surgery, Kansas City, MO., 1991, pp. 418-423.

Balzamo, E. et al., "Short-latency components of evokes potentials to median nerve stimulation recorded by intracerebral electrodes in the human pre- and postcentral areas", Clinical Neurophysiology, 2004, vol. 115, pp. 1616-1623.

Barberi, Enzo A. et al., "A Transmit-Only/Receive-Only (TORO) RF System for High-Field MRI/MRS Applications", Magnetic Resonance in Medicine, 2000, Vil. 43, pp. 284-289.

Beckmann, Christian F. et al., "Probabilistic Independent Component Analysis for Functional Magnetic Resonance Imaging", IEEE Transactions on medical Imaging, 2004, vol. 23, No. 2. pp. 137-152.

Bessho, H. et al., "Localization of Palatal Area in Human Somatosensory Cortex", J Dent Res, 2007, vol. 86, No. 3, pp. 265-270.

Boliek, C. A. et al., "Effect of age on salivary flow obtained under feeding and non-feeding conditions", Journal of Oral Rehabilitation, 2007, vol. 34, pp. 433-441.

Bourdiol, P. et al., "Establishing a reliable protocol to measure tongue sensation", Journal of Oral Rehabilitation, 2004, vol. 31, pp. 445-452.

Bove, Mogens et al., "Thermal Oral-Pharyngeal Stimulation and Elicitation of Swallowing", Acta Otolaryngol (Stochk), 1998, vol. 118. pp. 728-731.

Broekhuusen M. L. et al., "Factors Influencing jaw Position Sense In Man", Archs oral Biol., 1983, vol. 28, No. 5, pp. 387-391.

Calhoun, Karen K. et al., "Age-Related Changes in Oral Sensation", Laryngoscope, 1992, vol. 102, pp. 109-116.

Capra, Norman F., "Mechanism of Oral Sensation", Dysphagia, 1995, vol. 10, pp. 235-247.

Chamberlain, Cheryl K. et al., "Intra-oral tactile sensation and aging in a community-based population", Aging Clin Exp Res, 2006, vol. 19, No. 2, pp. 85-90.

Cook, I. J. et al., "Influence of aging on oral-pharyngeal bolus transit and clearance during swallowing: scintigraphic study", The American Physiological Society, 1994, pp. G972-G977.

Craig, A. D. et al., "Thermosensory activation of insular cortex", 2000, Nature Neuroscience, vol. 3, No. 2, pp. 184-190.

Dale et al. "Cortical Surface-Based Analysis", NeuroImage, 1999, vol. 9, pp. 179-194.

Darian-Smith, I. et al., "Somatic Sensory Cortical Projection Areas Excited By Tactile Stimulation Of The Cat: A Triple Representation", J. Physiol., 1966, vol. 182. pp. 671-689.

Dawes, C., "Circadian Rhythms in Human Salivary Flo Rate and Composition", J. Physiol., 1972, vol. 220. pp. 529-545.

Dawes, C. et al., "Circadian Rhythms In The Flow Rate and Proportional Contribution of Parotid To Whole Saliva Volume in Man", Archs oral Biol., 1973, vol. 18. pp. 1145-1153.

Ding, Ruiying et al., "The Effects of taste and Consistency on Swallow Physiology in Younger and Older Healthy Individuals: A Surface Electromyographic Study", Journal of Speech, Language, and Hearing Research, 2003, vol. 46, pp. 977-989.

Disbrow, Elizabeth A. et al., "Ipsilateral Representation of Oral Structures in Human Anterior Parietal Somatosensory Cortex and Integration of Inputs Across the Midline", The Journal of Comparative Neurology, 2003, vol. 467, pp. 487-495.

(56) References Cited

OTHER PUBLICATIONS

Do, David H. et al., "Resolving Subjects and Measuring Observer/Subject Distances with a Thermal Tactile Imager", IEEE, 30th Annual International IEEE EMBS Conference, Vancouver, Canada, 2008, pp. 4302-4305.

Doty, Robert W., "Influence of Stimulus pattern on Reflex Deglutition", Dept. Of Physiology, The University of Chicago, 1951, vol. 166, pp. 142-158.

Dum, Richard R. et al., "Motor areas in the frontal lobe of the primate", Physiology and Behavior, 2002, vol. 77, pp. 677-682.

Ettlin, D. A. et al., "Cortical Activation Resulting from Painless Vibrotactile Dental Stimulation Measured by Functional Magnetic Resonance Imaging (fMRI)", J. Dent Res.. 2004, vol. 83, No. 10. pp. 757-761.

Fabri, Mara et al., "Bulateral Cortical Representation of the Trunk Midline in Human First Somatic Sensory Area", Human Brain Mapping, 2005, vol. 25, pp. 287-296.

Ferguson D. B. et al., "Circadian Rhythms In Human Partotid Saliva Flow Rate and Composition", Archs oral Biol., 1973, vol. 18. pp. 1155-1173.

Flynn, Frederick et al., "Anatomy of the insula-functional clinical correlates", Aphasiology, 1999, vol. 13, No. 1, pp. 55-78.

Fraser, Chris et al., "Driving Plasticity in Human Adult Motor Cortex is Associated with Improved Motor Function after Brain Injury", Neuron, 2002, vol. 34, pp. 831-840.

Fujiu, Masako et al., "Glossopharyngeal evoked potentials in normal subjects following n=mechanical stimulation of the anterior faucial pillar", Electroencephalography and Clinical Neurophysiology, 1994, vol. 92, pp. 183-195.

Fukunaga, Akiko et al., "Influences of Aging on Taste Perception and Oral Somatic Sensation", Journal of Gerontology: Medical Sciences, 2005, vol. 60A, No. 1, pp. 109-113.

Gemba, Hisae et al., "Influences of emotion upon parotid secretion in human", Neuroscience Letters, 1996, vol. 211, pp. 159-162.

Gross, Roxann D. et al., "Lung Volume Effects On Pharyngeal Swallowing Physiology", J. Appl. Physiol, vol. 95, 2003, pp. 2211-2217.

Hamdy, Shaheen et al., "Cranial nerve modulation of human cortical swallowing motor pathways", American Physiological Society, 1997, pp. G802-G808.

Hamdy, Shaheen et al., "Explaining oropharyngeal dysphagia after unilateral hemispheric stroke", The Lancet, 1997, vol. 350, pp. 686-692.

Hamdy, Shaheen et al., "Long-term reorganization of human motor cortex driven by short-term sensory stimulation", Nature America Inc., 1998, vol. 1, No. 1, pp. 64-68.

Hamdy, S. et al., "Modulation of human swallowing behavior by thermal and chemical stimulation in health and after brain injury", Neurogastroenterology and Motility, 2003, vol. 15, pp. 69-77.

Hamdy, Shaheen et al., "Recovery of Swallowing After Dysphagic Stroke Relates to Functional Reorganization in the Intact Motor Cortex", Gastroenterology, 1998; vol. 115, No. 5, pp. 1104-1112.

Hamdy, Shaheen et al., "The cortical topography of human swallowing musculature in health and disease", Nature Medicine, 1996, vol. 2, No. 11, pp. 1217-1224.

Hayashi, H. et al., "Functional Organization of Trigeminal Subnucleus Interpolaris: Nociceptive and Innocuous Afferent Inputs, Projections to Thalamus, Cerebellum, and Spinal Cord, and Descending Modulation From Periaqueductal Gray", The American Physiological Society, Journal of Neurophysiology, 1984, vol. 51, No. 5, pp. 890-905.

Hiraba, Hisao et al., "Increased Secretion of Salivary Glands Produced By Facial Vibrotactile", Somatosensory and Motor Research, vol. 25, 2008, pp. 222-229.

Huang, C.-S. et al., "Input-Output Relationships of the Primary Face Motor Cortex in the Monkey (Macaca fascicularis)", The American Physiological Society, Journal of Neurophysiology, 1989, vol. 61, No. 2, pp. 350-362.

Iwamura, Yoshiaki et al., "Bilateral Activity and Callosal Connections in the Somatosensory Cortex", The Neuroscientist, 2001, vol. 7, No. 5, pp. 419-429.

Iyengar, Soumya et al., "Cortical and Thalamic Connections of the Representations of the Teeth and Tongue on Somatosensory Cortex of New World Monkeys", The Journal of Comparative Neurology, 2007, vol. 501, pp. 95-120.

Jacobs, Reinhilde et al., "Oral stereognosis: a review of the literature", Clin Oral Invest, 1998, vol. 2, pp. 3-10.

Jafari, Samah et al., "Sensory Regulation of Swallowing and Airway Protection: A Role For The Internal Superior Layngeal Nerve In Humans", J. Physiol, vol. 550, No. 1, 2003. pp. 287-304.

Jafary, Samah et al., "Sensory regulation of swallowing and airway protection: a role for the internal superior laryngeal nerve in humans", The physiological Society, J Physiol, 2003, vol. 30, No. 10, pp. 1-18.

Jain, Neeraj et al., "Anatomic Correlates of the face and Oral Cavity Representations in the Somatosensory Cortical Area 3b Monkeys", The Journal of Comparative Neurology, 2001, vol. 429, pp. 455-468.

Jaradeh, Safwan, MD, "Neurophysiology of Swallowing in the Aged", Dysphagia, 1994, vol. 9, pp. 218-220.

Jean, Andre, "Brain Stem Control of Swallowing: Neuronal Network and Cellular Mechanisms", The American Physiological Society, 2001, vol. 81, No. 2, pp. 929-969.

Jean, Andre et al., "Inputs to the swallowing medullary from the peripheral afferent fibers and the swallowing cortical area", Brain Research, 1979, vol. 178, pp. 567-572.

Jobin, Vincent et al., "Swallowing function and upper airway sensation in obstructive sleep apnea", J. Appl. Physiol., 2007, vol. 102, pp. 1587-1594.

Kaatzke-McDonald, Monika N., M App Sc et al., "The Effects of Cold, Touch, and Chemical Stimulation of the Anterior Faucial Pillar on Human Swallowing", Dysphagia, 1996, vol. 11, pp. 198-206.

Kapila, Yagya V., MD et al., "Relationship Between Swallow Rate and Salivary Flow", Digestive Diseases and Sciences, 1984, vol. 29, No. 6, pp. 528-533.

Kern, Mark K. et al., "Cerebral cortical representation of reflexive and volitional swallowing in humans", American Physiological Society, Am J Physiol Gastrointest Liver Physiol, 2001, vol. 280, pp. G354-G360.

Kim, Il Soo et al., "Influence of Mastication and Salivation on Swallowing in Stroke Patients", Arch Phys Med Rehabil, 2005, vol. 86, pp. 1986-1990.

Kitagawa, Jun-Ichi et al., "Pharyngeal branch of the glossopharyngeal nerve plays a major role in reflex swallowing from the pharynx", American Physiological Society, Am J Physiol Regulatory Integrative Comp Physiol, 2002, vol. 282, pp. R1342-R1347.

Kleim, Jeffrey A. et al., "Principles of Experience-Dependent Neural Plasticity: Implications for Rehabilitation After Brain Damage", Journal of Speech, Language, and Hearing Research, 2008, vol. 51, pp. S225-S239.

Lagerlöf, F. et al., "The Volume of Saliva in the Mouth Before and After Swallowing", Univ of Western Ontario, 2009, vol. 63, No. 5, pp. 618-621.

Lazzara, Gisela de Lama, M.A. et al., "Impact of Thermal Stimulation on the Triggering of the Swallowing Reflex", Dysphagia, 1986, vol. 1, pp. 73-77.

Lear, C. S. C. et al., "The Frequency of Deglutition In Man", Arch. oral Biol., 1965, vol. 10, pp. 83-99.

Lim, Kil-Byung, MD, PhD et al., "Neuromuscular Electrical And Thermal-Tactile Stimulation For Dysphagia Caused By Stroke: A Randomized Controlled Trial", J Rehabil Med, 2009, vol. 41, pp. 174-178.

Lin, L.-D. et al., "Functional Properties of Single Neurons in the Primate Face Primary Somatosensory Cortex. II. Relations With Different Directions of Trained Tongue Protrusion", The American Physiological Society, Journal of Neurophysiology, 1994, vol. 71, No. 6, pp. 2391-2400.

Linden, Patricia, M.A. et al. "Bolus Position at Swallow Onset in Normal Adults: Preliminary Observations", Dysphagia, 1989, vol. 4, pp. 146-150.

(56) References Cited

OTHER PUBLICATIONS

Logemann, Jeri A. et al., "Closure mechanisms of laryngeal vestibule during swallow", The American Physiological Society, Am. J. Physiol., 1992, vol. 262, pp. G338-G344.
Logemann, Jeri et al., "Effects of a Sour Bolus on Oropharyngeal Swallowing Measures in Patients With Neurogenic Dysphagia", Journal of Speech and Hearing Research, 1995, vol. 35, pp. 556-563.
Logemann, Jeri A., Ph.D., "Preswallow Sensory Input: Its Potential Importance to Dysphagic Patients and Normal Individuals", Dysphagia, 1996, vol. 11, pp. 9-10.
Logemann, Jeri A. et al., "Temporal and Biomechanical Characteristics of Oropharyngeal Swallow in Younger and Older Men", American Speech Language-Hearing Association, Journal of Speech, Language, and Hearing Research, 2000, vol. 43, pp. 1264-1274.
Logemann, Jeri A., "The Effects of VitalStim on Clinical Research Thinking in Dysphagia", Dysphagia, No. 22, 2007, pp. 11-12.
Lowell, SY et al., Abstract titled "Cerebral activation patterns during swallowing and related tasks using functional magnetic resonance imaging," Dysphagia, vol. 22, 2007, p. 401, 2 pages.
Lowell, Soren et al., "Sensory Stimulation Activates Both Motor and Sensory Components of the Swallow System", NeuroImage, vol. 42, 2008, pp. 285-295.
Lowell, Soren et al., "The Effects of Sensory Stimulation on Urge and Frequency of Swallowing", PPT Presentation made at the 2008 meeting of the Dysphagia Research Society, National Institutes of Health, 2008, 14 pgs.
Malenfant, Annie et al., "Tactile, thermal and pain sensibility in burned patients with and without chronic pain and paresthesia problems", International Association for the Study of Pain, 1998, vol. 77, pp. 241-251.
Manger, Paul R. et al., "Representation of Face and Intra-Oral Structures in Area 3b of Macaque Monkey Somatosensory Cortex", The Journal of Comparative Nurology, 1996, vol. 371, pp. 513-521.
Månsson, Ingemar, M.D. et al., "Effects of Surface Anesthesia on Deglutition In Man", Department of Otorhinolaryngology, University of Gothenburg, Sweden, 1973-1974, pp. 427-437.
Marik, Paul E., MD, FCCP et al., "Aspiration Pneumonia and Dysphagia in the Elderly", American College of Chest Physicians, Chest, 2003, vol. 124, pp. 328-336.
Martin, Ruth E. et al., "Cerebral Areas Processing Swallowing and Tongue Movement Are Overlapping but Distinct: A Functional Magnetic Resonance Imaging Study", The American Physiological Society, J Neurophysiol, 2004, vol. 92, pp. 2428-2443.
Martin, Ruth et al., "Cerebral cortical processing of swallowing in older adults", Exp Brain Res, 2007, vol. 176, pp. 12-22.
Martin, Ruth E. et al., "Cerebral Cortical Representation of Automatic and Volitional Swallowing in Humans", The American Physiological Society, J Neurophysiol, 2001, vol. 85, pp. 938-950, www.jn.physiology.org.
Martin, Ruth E. et al., "Features of Cortically Evoked Swallowing in the Awake Primate (*Macaca fascicularis*)", The American Physiological Society, J. Neurophysiol., 1999, vol. 82, pp. 1529-1541.
Martin, Ruth E. et al., "Functional Properties of Neurons in the Primate Tongue Primary Motor Cortex During Swallowing", The American Physiological Society, 2007, pp. 1516-1530.
Martin, Ruth E., "Neuroplasticity and Swallowing", Dysphagia, 2008.
Martin, Ruth E. et al., "The Role of the Cerebral Cortex in Swallowing", Dysphagia, 1993, vol. 8, pp. 195-202.
McKee, G. J. et al., "Does age or sex affect pharyngeal swallowing?", Clinical Otolaryngology, 1998, vol. 23, pp. 100-106.
Menon, Ravi S., "Postacquisition Suppression of Large-Vessel BOLD Signals in High-Resolution fMRI", Magnetic Resonance in Medicine, 2002, vol. 47, pp. 1-9.
Mese, H. et al., "Invited Review—Salivary secretion, taste and hyposalivation", Journal of Oral Rehabilitation, 2007, vol. 34, pp. 711-723.

Miller, Arthur J., "Deglutition", Physiological Reviews, 1982. vol. 62, No. 1, pp. 129-184.
Miyamoto, Jun J. et al., "The Representation of the Human Oral Area in the Somatosensory Cortex: a Functional MRI Study", Cerebral Cortex, 2006, vol. 16, No. 5, pp. 669-675.
Mizobuchi, Keiko et al., "Single unit responses of human cutaneous mechanoreceptors to air-puff stimulation", Clinical Neurophysiology, 2000, vol. 111, pp. 1577-1581.
Mosier, Kristine, DMD, PhD et al., "Cortical Representation of Swallowing in Normal Adults: Functional Implications", The American Laryngological, Rhinological and Otological Society, Inc., The Laryngoscope, 1999, vol. 109, pp. 1417-1423.
Mu, Liancai et al., "Sensory Nerve Supply of the Human Oro- and Laryngopharynx: A Preliminary Study", The anatomical Record, 2000, vol. 258, pp. 406-420.
Murray, Joseph et al., "The Significance of Accumulated Oropharyngeal Secretions and Swallowing Frequency in Predicting Aspiration", Dysphagia, 1996, vol. 11, pp. 99-103.
Nakamura, Akinori et al., "Somatosensory Homunculus as Drawn by MEG", NeuroImage, 1998, vol. 7, pp. 377-386, Article No. NI980332.
Navazesh, M. et al., "A Comparison of Whole Mouth Resting and Stimulated Salivary Measurement Procedures", J Dent Res, 1982, vol. 61, No. 10, pp. 1158-1162.
Nguyen, Anh Tu et al., "Laryngeal and Velopharyngeal Sensory Impairment in Obstructive Sleep Apnea", Sleep, 2005, vol. 28, No. 5, pp. 585-593.
Ootani, Shinji et al., "Convergence of Afferents from the SLN and GPN in Cat Medullary Swallowing Neurons", Brain Research Bulletin, 1995, vol. 37, No. 4, pp. 397-404.
Palmer, Jeffrey B., M.D. et al., "Coordination of Mastication and Swallowing", Dysphagia, 1992, vol. 7, pp. 187-200.
Pommerenke, W. T., "A Study Of The Sensory Areas Eliciting The Swallowing Reflex", The American Journal of Physiology, 1927, vol. 81, No. 1, pp. 36-41.
Power, M. et al., "Changes in pharyngeal corticobulbar excitability and swallowing behavior after oral stimulation", Am J. Physiol Garstrointest Liver Physiol, 2004, vol. 286 pp. G45-G50.
Power, Macine L., PhD et al., "Evaluating Oral Stimulation as a Treatment for Dysphagia after Stroke", Dysphagia, 2006, pp. 49-55.
Robbins, JoAnne et al., "Swallowing After Unilateral Stroke of the Cerebral Cortex Preliminary Experience", Dysphagia, 1988, vol. 3, pp. 11-17.
Robbins, JoAnne et al., "Swallowing and Dysphagia Rehabilitation: Translating Principles of Neural Plasticity Into Clinically Oriented Evidence", American Speech-Language-Hearing Association, Journal of Speech, Language, and Hearing Research, 2008, vol. 51, pp. S276-S300.
Rosenbek, John C., PhD et al., "Comparing Treatment Intensities of Tactile-Thermal Application", Dysphagia, 1998, vol. 13, pp. 1-9.
Rosenbeck, John C. et al., "Effects of Thermal Application on Dysphagia After Stroke", Journal of Speech and Hearing Research, 1991, vol. 34, pp. 1257-1268.
Rosenbek, John C., PhD et al., "Thermal Application Reduces the Duration of Stage Transition in Dysphagia after Stroke", Dysphagia, 1996, vol. 11, pp. 225-233.
Ruben, J. et al., "Somatotopic Organization of Human Secondary Somatosensory Cortex", Cerebral Cortex, 2001, vol. 11, No. 5, pp. 463-473.
Rudney, J. D. et al., "The Prediction of Saliva Swallowing Frequency in Humans From Estimates of Salivary Flow Rate and The Volume of Saliva Swallowed", Archs oral Biol., 1995, vol. 40, No. 6, pp. 507-512.
Schneyer, Leon H. et al., "Rate of Flow of Human Parotid, Sublingual, and Submaxillary Secretions During Sleep", J. D. Res., 1956, vol. 35, No. 1, pp. 109-114.
Sciortino, Kellie Filter, PhD, CCC-SLP et al., "Effects of Mechanical, Cold, Gustatory, and Combined Stimulation to the Human Anterior Faucial Pillars", Dysphagia, 2003, vol. 18, pp. 16-26.
Servos, Philip et al., "fMRI evidence for an inverted face representation in human somatosensory cortex", NeuroReport, 1999, vol. 10, No. 7, pp. 1393-1395.

(56) References Cited

OTHER PUBLICATIONS

Sessle, Barry J. et al., "Cortical mechanisms controlling mastication and swallowing in the awake monkey", Brain and oral Functions, Published by Elsevier Science B.V. 1995, pp. 181-189.
Sessle, B. J., "Review Article, Mechanisms of oral somatosensory and motor functions and their clinical correlates", Journal of Oral Rehabilitation, 2006, vol. 33, pp. 243-261.
Shaffer, Scott W. et al., "Aging of the Somatosensory System: A translational Perspective", American Physical Therapy Association, 2007, vol. 87, No. 2, pp. 193-207.
Shaw, D. W. et al., "Influence of normal aging on oral-pharyngeal and upper esophageal sphincter function during swallowing", American Physiological Society, Am. J. Physiol., 1995, vol. 268, pp. G389-G396.
Ship, Jonathan A., DMD et al., "Xerostomia and The Geriatric Patient", Journal of American Geriatric Society, 2002, vol. 50, No. 3, pp. 535-543.
Simon, Sidney A. et al., "The neural mechanisms of gestation: a distributed processing code", Nature Reviews, Neuroscience, 2006, vol. 7, pp. 890-901.
Sinclair, William J., "Role of the pharyngeal plexus in initiation of swallowing", American Journal of Physiology, 1971, vol. 221, No. 5, pp. 1260-1263.
Smith, Stephen M., "Fast Robust Automated Brain Extraction", Human Brain Mapping, 2002, vol. 17, pp. 143-155.
Sonies, Barbara C., Ph.D. et al., "Durational Aspects of the Oral-Pharyngeal Phase of Swallow in Normal Adults", Dysphagia, 1988, vol. 3, pp. 1-10.
Sörös, Peter et al., "Clustered functional MRI of overt speech production", NeuroImage, 2006, vol. 32, pp. 376-387.
Sörös, P. et al., "Functional MRI of Oropharyngeal Air-Pulse Stimulation", Neuroscience, 2008, vol. 153, pp. 1300-1308.
Sörös, Peter et al., "Research article, Functional MRI of working memory and selective attention in vibrotactile frequency discrimination", BMC Neuroscience, 2007, vol. 8, No. 48, pp. 1-10.
Sörös, P. et al., "Functional MRI of Oropharyngeal Air-Pulse Stimulation", Neuroscience, vol. 53, 2008, pp. 1300-1308.
Stephen, Jennifer R., MSc et al., "Bolus Location at the Initiation of the Pharyngeal Stage of Swallowing in Healthy Older Adults", Dysphagia, 2005, vol. 20, pp. 266-272.
Tanji, J. et al., "Submodality Distribution in Sensorimotor Cortex of the Unanesthetized Monkey", Journal of Neurophysiology, 1981, vol. 45, No. 3, pp. 467-481.
Taoka, Miki et al., "Representation of the midline trunk, bilateral arms, and shoulders in the monkey postcentral somatosensory cortex", Exp Brain Res, 1998, vol. 123, pp. 315-322.
Theurer, Julie A., MCISc et al., "Oropharyngeal Stimulation with Air-Pulse Trains Increases Swallowing Frequency in Healthy Adults", Dysphagia, 2005, vol. 20, pp. 254-260.
Theurer, Julie et al., "The Effects of Oropharyngeal Air-Pulse Stimulation on Swallowing in Healthy Older Adults", Dysphagia, 2009, 12 pgs.
Tracy, Julie F., M.A. et al., "Preliminary Observations on the Effects of Age on Oropharyngeal Deglutition", Dysphagia, 1989, vol. 4, pp. 90-94.
Unknown author, Program of the 103rd Meeting of the Acoustical Society of America, J. Acoust. Am., 1982, Suppl. 1, vol. 71 pp. S1-S113.
Unknown author, Brochure, Pentax, ENT Scopes, 2005, 2 pgs.
Van Willigen, J. D. et al., "On the Self-Perception Of Jaw Positions In Man", Archs oral Biol., 1983, vol. 28, No. 2, pp. 17-122.
Vandenbergh, Joris et al., "Regional Brain Activation During Proximal Stomach Distention in Humans: A Positron Emission Tomography Study", American Gastroenterological Association, 2005, vol. 128, pp. 564-573.
Woolrich, Mark W. et al., "Multilevel linear modeling for FMRI group analysis using Bayesian inference", NeuroImage, 2004, vol. 21, pp. 1732-1747.
Yamamoto, Takashi et al., "Taste Responses of Cortical Neurons in Freely Ingesting Rats", Journal of Neurophysiology, 1989, vol. 61, No. 6, pp. 1244-1258.
Yamashita, H. et al., "Magnetic sensory cortical responses evoked by tactile stimulations of the human face, oral cavity and flap reconstructions of the tongue", Eur Arch Otorhinolaryngol, 1999, vol. 256, pp. S42-S46.
Yoshida, Yoshikazu, MD et al., "Sensory Innervation of the Pharynx and Larynx", The American Journal of Medicine, 2000, vol. 108 (4A), pp. 51S-61S.
Yoshida, Kazuya et al., "Somatosensory evoked magnetic fields to air-puff stimulation on the soft palate", Neuroscience Research, 2006, vol. 55, pp. 116-122.
Zald, David H. et al., "Cortical Activation Induced by Intraoral Stimulation with Water in Humans", Chem. Senses, 2000, vol. 25, pp. 267-275. Abstracts.
Freed M. L. et al., "Electrical stimulation for swallowing disorders caused by stroke", Respir care, 2001, vol. 46, No. 5, p. 466.
Rosenbek, J. C. et al., "Effects of thermal application on dysphgia after stroke", J Speech Hear Res, 1991, vol. 34, No. 6, pp. 1257.

\* cited by examiner

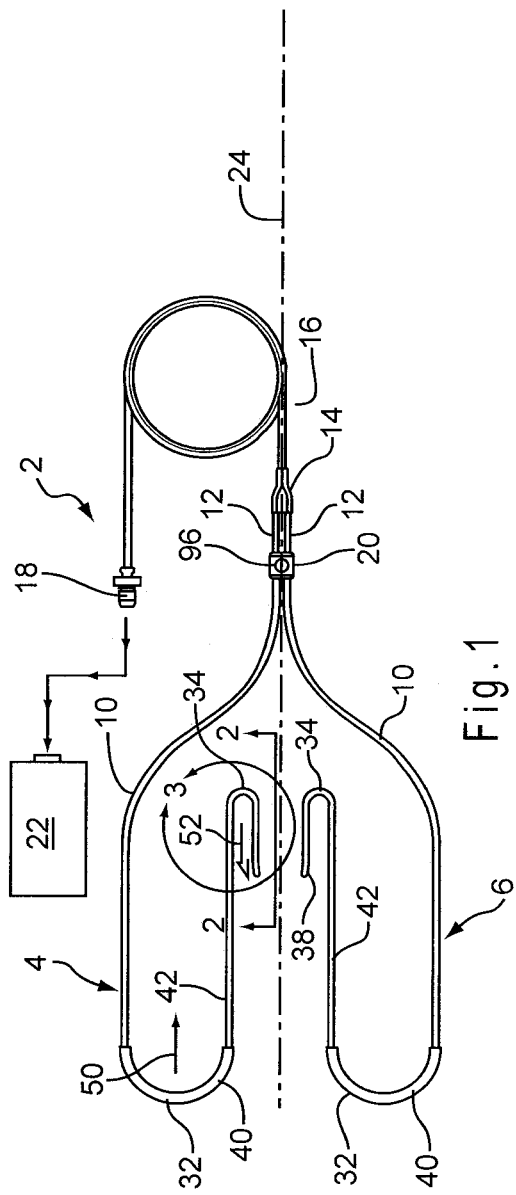
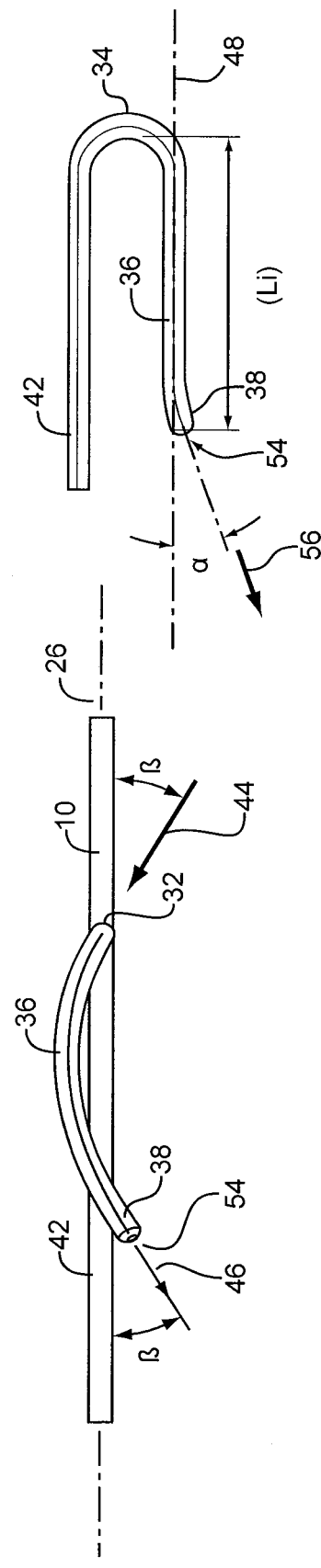
Fig. 1
Fig. 2
Fig. 3

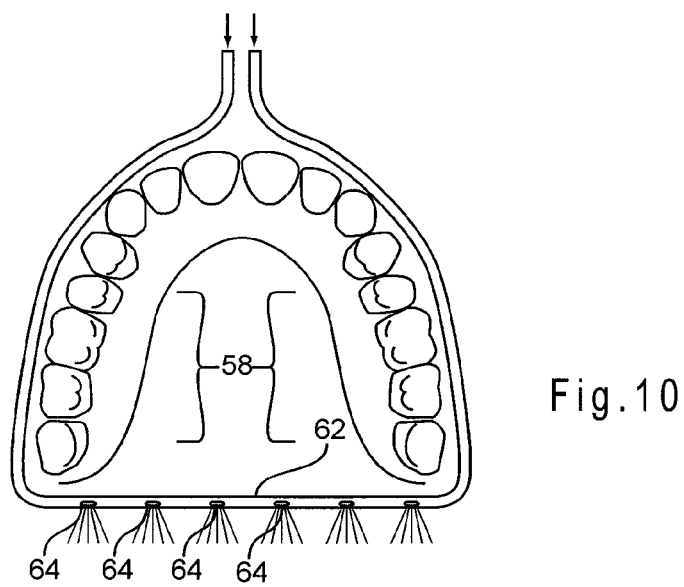
Fig.10
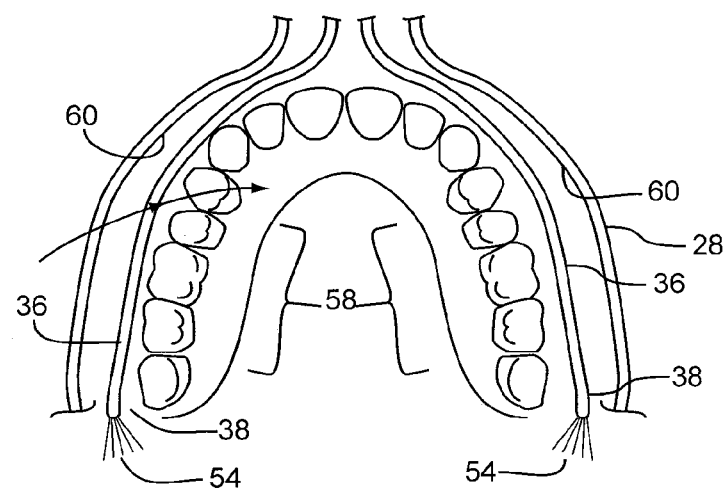
Fig.11
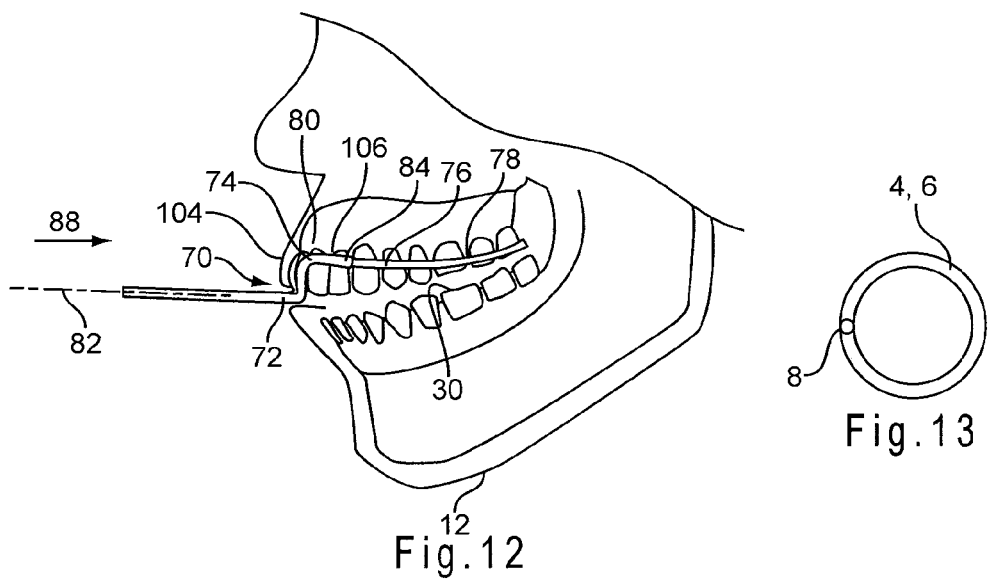
Fig.12
Fig.13

Intracortical microstimulation of the lateral primary motor cortex.

Functional magnetic resonance imaging of swallowing, tongue elevation, and finger opposition.

Swallowing rate in a patient with stroke.

Functional magnetic resonance imaging of oropharyngeal air-pulse stimulation.

Functional magnetic resonance imaging of air-pulse induced swallowing.

SWALLOWING AIR PULSE THERAPY MOUTHPIECE AND METHOD FOR THE USE THEREOF

This application is a continuation of U.S. application Ser. No. 12/424,191, filed Apr. 15, 2009, which application claims the benefit of U.S. Provisional Patent Application No. 61/071,144, entitled Swallowing Air Pulse Therapy Mouthpiece and Method for the Use Thereof and filed Apr. 15, 2008, the entire disclosures of which are hereby incorporated herein by reference.

TECHNICAL FIELD

The present invention relates generally to an oral appliance used to administer a stimulus to a human or animal to elicit and/or facilitate a desired physiological response and in particular, to a mouthpiece for delivering a substance to a human or animal to elicit and/or facilitate swallowing and a method for the use thereof.

BACKGROUND

Dysphagia is a condition in which a person has difficulty swallowing, characterized by impaired transport of saliva, drink, and food from mouth to stomach. Dysphagia results from disease, or damage, to the neural and/or aerodigestive tract structures that produce swallowing (Logemann, 1998). Often, dysphagia presents in stroke patients, patients with other acute neurological conditions, patients having Parkinson's disease or other neurodegenerative diseases, cerebral palsy or chronic obstructive pulmonary disease (COPD) and/or in response to various cancer treatments, wherein the patient has difficulty in, and/or experiences pain with, swallowing. Likewise, other patients may exhibit various swallowing, speech, salivary and/or oral sensory impairments. Dysphagia compounds these health problems via resultant complications, most commonly aspiration pneumonia secondary to entry of saliva or food into the lungs, dehydration and malnutrition (Smithard et al., 1996). As such, some deaths attributed to stroke, may actually be caused by dysphagia and the resulting complication of pneumonia. These complications may also lead to extended hospital stays, emergency room visits, re-admissions, long-term institutional care and need for expensive respiratory and nutritional support. The cost of dysphagia to North American health care systems is estimated to exceed 1 billion USD annually (Agency for Health Care Research and Quality, US Centers for Disease Control and Prevention). Moreover, because dysphagia is most common among the elderly, its prevalence will increase as the population ages over the next 40 years.

In response, various techniques and treatments have been developed to induce or stimulate swallowing, which can provide various therapeutic benefits to the patient or user. For example, as disclosed in US Pub. No. 2006/0282010A1, entitled Oral Device (the entirety of which is hereby incorporated herein by reference), a device and method for inducing swallowing in a patient includes delivering one or more gas pulses to a predetermined area of the mouth and/or throat. The delivery device includes a molded dental splint that is fitted over the patient's lower teeth and is disposed between the teeth of the user.

Another swallowing therapy is VitalStim, which applies electrical stimulation to the neck overlying the laryngeal muscles with the goal of augmenting laryngeal elevation during swallowing (Freed et al. 2001).

SUMMARY

The present invention is defined by the following claims, and nothing in this section should be considered to be a limitation on those claims.

In a first aspect, one embodiment of an oral appliance for delivering a substance to the mouth of a user includes a flexible tube having an inlet portion, a first curved portion forming an ear loop connected to the inlet portion, a second curved portion forming a lip bend connected to the first curved portion, and an outlet portion extending from the second curved portion. In one embodiment, the outlet portion may also include a third curved portion and an end portion having a gas exit port. In one embodiment, the end portion is also curved. In one embodiment, the first and second curved portions may have a curvature in a first plane, and the third curved portion may have a curvature in a second plane non-parallel to the first plane.

In one embodiment, the oral appliance includes a second tube portion also having an ear loop, lip bend and gas exit port. The inlet portions of the first and second tube portions can be connected. In one embodiment, the outlet portions of the first and second tube portions are connected by a manifold.

In another embodiment, an oral appliance for delivering a substance to the mouth of a user includes a housing having an inlet portion, a riser portion extending upwardly from the inlet portion and a curved outlet portion. The outlet portion has a pair of branches extending laterally outwardly from the riser portion. A flexible tube is coupled to the housing and extends through the inlet portion, the riser portion and out of at least one of the branches of the outlet portion. The flexible tube has an end portion extending from the outlet portion of the housing. The end portion has a fluid exit port positioned downstream of the outlet portion of the housing. In one embodiment, the curved outlet portion may have a first curvature when viewing the curved outlet portion from a first direction. The curved outlet portion may also have a second curvature when viewing the curved outlet portion from a second direction, wherein the first and second directions are non-parallel.

In another aspect, a method of delivering a substance to a predetermined location in a user's mouth includes disposing a flexible tube between an outer side of a row of teeth and an inner surface of a cheek. The flexible tube has an exit port positioned in a rear region of the mouth. No portion of the flexible tube is disposed between the upper and lower teeth of the user such that the upper and lower teeth can be closed against each other or in close approximation to each other. The method further includes dispensing a substance through the exit port. Various embodiments of the method may also include disposing a curved portion of the flexible tube around an ear of the user, and/or disposing a curved portion around a lip of the user. In various embodiments, the flexible tube may be disposed between lateral surfaces of lower teeth and the cheek of the user, or between lateral surfaces of upper teeth and the cheek of the user. In one embodiment, orientation indicia may be provided to instruct the user about the proper orientation of the device relative to the user and/or substance supply/control unit.

In yet another aspect, a method for assembling a substance delivery device includes forming the flexible tube, for example to define an ear loop, lip bend and curved end portion. The method of assembling may include fitting a tube within a channel formed in a housing.

The various aspects and embodiments provide significant advantages relative to the prior known devices. In particular, the oral appliance can be made easily and quickly without having to customize the device to a particular user. The flexible tube follows the natural contours of the user's face and mouth. Moreover, the flexible tube is self-supporting in the preferred location in the user's mouth, and is maintained in a proper position even with patients/users experiencing numbness or weakness of the lips, tongue or jaw. The device is not fitted over or between the user's upper and lower teeth, and does not have to be held in place by specific jaw positioning. In this way, the flexible tubing, which is disposed between the user's teeth and cheek, does not interfere with normal speech, eating, drinking swallowing, etc., or with the fluid pulse delivery and swallowing therapy.

In addition, the oral appliance and method for the use thereof does not require the patient to follow instructions or produce voluntary movements of the mouth. Rather, the therapy involves the delivery of a train of at least one pulse of a substance to the patient, who is a passive recipient. This can be important since patients at risk of dysphagia may be unable to follow complex instructions or produce voluntary movements. In another aspect, however, the therapy can be applied in association with voluntary attempts to swallow by a patient. In other aspects, the therapy can be used to enhance behavioral therapy, for example, by providing information about the swallow, obtained from physiological recordings, to the patient, as a form of (bio)feedback. In addition, patients do not need to be able to eat by mouth, meaning they can receive the therapy when a nasogastric or gastrostomy tube is in place. In addition, the mouthpiece and method can be used outside of a clinical setting, for example at home, which has advantages over other types of therapy such a VitalStim. Moreover, the device is relatively non-invasive, and does not require any intrusion through the patient's nose and pharynx.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIG. 1 is a plan view of a first embodiment of an oral appliance.

FIG. 2 is a partial side view of the oral appliance shown in FIG. 1 taking along line 2-2.

FIG. 3 is a partial, enlarged view of the oral appliance shown in FIG. 1.

FIG. 10 is a plan view of a third embodiment of an oral appliance positioned in the mouth of the user.

FIG. 11 is a partial plan view of portions of an oral appliance disposed in the mouth of the user.

FIG. 12 is a partial, side cross-sectional view of the oral appliance of FIG. 6 disposed in the mouth of a user.

FIG. 13 is an enlarged, cross-sectional view of one embodiment of a tube.

DETAILED DESCRIPTION OF THE DRAWINGS

Figure 4:
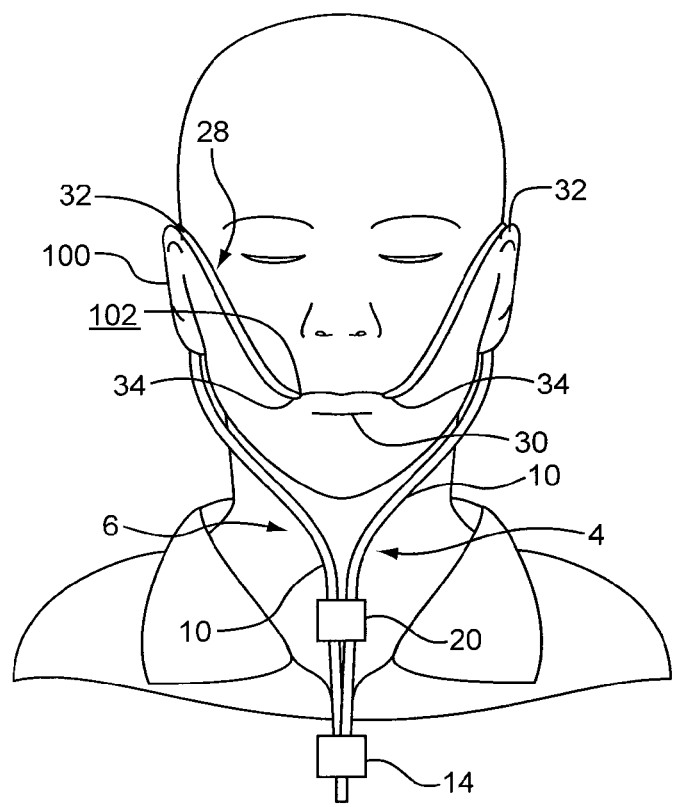
FIG. 4 is a front view of a user with the oral appliance of FIG. 1 located in an operational position.

The terms "top," "bottom," "upwardly" and "downwardly" are intended to indicate directions when viewing the oral appliance from the perspective of the user. The term "lateral," as used in this application, means situated on, directed toward or running from side-to-side, for example and without limitation from one side of the user's mouth to the other. It should be understood that the term "plurality," as used in this application, means two or more. The term "longitudinal," as used in this application means of or relating to length or the lengthwise direction. The term "coupled" as used in this application means connected to or engaged with whether directly or indirectly, for example with an intervening member, and does not require the engagement to be fixed or permanent, although it may be fixed or permanent, and includes both mechanical and electrical connection. It should be understood that the term "substance" as used in this application includes without limitation a fluid, such as a gas, liquid or combination thereof (including an aerosolized liquid), and/or a powder, including particles entrained in any fluid, or combinations thereof. The terms "includes" and "including" as used in this application mean includes and including without limitation.

As disclosed herein, a method and apparatus are provided for delivering or applying at least one uni-modal or multi-modal sensory stimulus to the receptive field(s) of at least one sensory cranial nerve within the oral cavity, oropharynx, and pharynx of a human or other animal for the purpose of (1) initiating, evoking or facilitating swallowing, speech production, salivation, or an oral or oropharyngeal sensorimotor behaviour in a subject, (2) increasing lubrication of the oral cavity, oropharynx, and pharynx in a subject, (3) decreasing oral or oropharyngeal or pharyngeal discomfort in a subject, (4) contraction of muscles of the lips, mouth, buccal area, tongue, jaw, soft palate, pharynx, larynx, any of which could result in muscle strengthening with repeated use of the oral appliance; (5) movement of the lips, mouth, buccal area, tongue, jaw, soft palate, pharynx, larynx, including elevation of the larynx, including pre-swallow oral transport movements and pre-swallow chewing-like movements; and/or (6) sensations from the oral cavity or oropharynx that include somatic, thermal or gustatory sensations. For example, the Swallowing Air-Pulse Therapy (SWAPT) embodiments disclosed herein maximize SWAPT-related swallowing facilitation by delivering multi-modal sensory stimulation to the subject; by reducing a subject's adaptation to the SWAPT sensory stimulus by altering the parameters of the SWAPT stimulus over time; or by applying SWAPT in association with voluntary preparation to perform a behavior, for example, preparing to swallow, or actual execution of a sensorimotor behavior performed by a person/patient such that the facilitatory effects of SWAPT act as a conditioning stimulus for the subsequent sensorimotor behavior. These effects are achieved through various embodiments namely: SWAPT with aerosol; various SWAPT mouthpiece embodiments; SWAPT with gustatory stimuli; SWAPT with thermal stimuli; and/or SWAPT with electrical stimulation or kinetic stimulation, and/or combinations thereof, and methods for delivering (i.e., triggering) SWAPT in association with a sensorimotor behaviour performed by a patient/subject. The application can be performed by direct contact with the tissues within which sensory receptors are located in the mouth or oropharynx of a human or animal or indirectly by delivering a substance that comes into direct contact with tissues within which sensory receptors are located in the mouth or oropharynx of a human or animal. Examples of direct contact includes without limitation placing the oral appliance in direct contact with an area of the mouth of a human or animal such that the appliance excites sensory receptors located within the contacted oral tissues and structures and by a kinetic effect within the oral appliance or a part thereof, for example, vibration or by applying an electrical current to such an area. Examples of indirect contact include without limitation delivering a fluid, such as a gas, liquid or aerosolized liquid, or a powder to an area in the mouth or oropharynx of a human or animal that includes sensory receptive fields.

The SWAPT embodiments disclosed herein generalize SWAPT-related swallowing facilitation by: providing a means of establishing an association between the SWAPT sensory stimulation and a sensorimotor response (skill) such that the swallowing reflexogenic properties of the SWAPT stimulus are, over training with SWAPT, assumed by the sensorimotor response alone through a process of conditioning; or providing a means of using SWAPT during eating, thereby generalizing SWAPT beyond saliva swallowing to prandial swallowing. These effects may be achieved through various embodiments, including methods for delivering (i.e., triggering) SWAPT in association with a sensorimotor behavior performed by a subject, for example, triggering SWAPT in relation to points within the respiratory cycle, in relation to swallowing preparation, or in relation to an attempt to swallow; and methods for delivering SWAPT to a subject patient during drinking and eating of liquids and solid foods.

Stimuli applied over the receptive field of the superior laryngeal nerve (SLN) are effective in evoking pharyngeal swallowing (Doty, 1968; Miller, 1999). Activating sensory fibers, of the glossopharyngeal nerve (IX) also evokes pharyngeal swallowing, but at higher thresholds (Sinclair, 1970). Sensory inputs to receptive fields innervated by both the IX and SLN are believed to be the most effective in evoking pharyngeal swallowing (Miller, 1999). Thus, swallowing therapies that stimulate receptive fields innervated by both the glossopharyngeal and SLN are expected to have a greater facilitatory effect on swallowing than therapies that excite only IX sensory fibers, or only SLN sensory fibers. Consistent with this, in one embodiment, SWAPT delivers air pulses (and/or aerosol) to receptive fields innervated by both the IX and SLN. This is a physiologically-based advantage of SWAPT that is not shared by other technologies that stimulate either the IX receptive field, or the SLN receptive field, but not both. Thus, a method is provided for simultaneously, or sequentially, stimulating the receptive fields of both the IX and SLN.

Mechanosensitive sensory fibers of the oral and pharyngeal regions synapse primarily in the trigeminal sensory nucleus within the brainstem, with fewer synapsing in the nucleus tractus solitariuus (NTS). The NTS is the anatomic location of the so-called "brainstem swallowing centre", the bilateral neural network within the brainstem that programs and orchestrates execution of the pharyngeal swallow (Jean, 2001). Taste-receptive sensory fibers (including water receptors) synapse primarily in the NTS. Although oral, pharyngeal, and laryngeal sensory inputs synapse in both the trigeminal sensory nucleus and the NTS, only sensory inputs to the NTS (and its surrounding reticular formation) initiate swallowing. Neurons within the NTS are multimodal, that is, they are excited by multiple sensory modalities (e.g., mechanical, gustatory, thermal) (Dubner, Sessle, Storey, 1978; Miller, 1999). Thus, the facilitatory effect of a sensory input of one modality is expected to summate with the facilitatory effects of sensory inputs of other modalities in terms of leading to action potentials that give rise to triggering of the brainstem swallowing centre and subsequent pharyngeal swallow. One embodiment of SWAPT provides the advantage of delivering multi-modal sensory stimulation to the oropharynx or mouth of a person. That is, the SWAPT air-pulse trains represent both mechanical and thermal stimulation. Evidence supporting the thermal property of the SWAPT air-pulse train is found in our study by Theurer et al. (2005) in which healthy controls reported that the oropharyngeal air-pulse trains were perceived as cool. Potential mechanisms for this thermal sensory effect are described below.

A moving stimulus applied to a given region of the oropharynx evokes a particular reflex (e.g., swallow, gag, etc.) depending on the pattern of movement (e.g., the type of movement, movement direction, movement velocity). Sensory stimulation with distilled water to receptive fields innervated by the glossopharyngeal (IX) nerve evokes swallowing in the anesthetized cat (Ootani et al., 1995). Water applied to the pharynx is effective as a stimulus for pharyngeal swallowing in humans (Nichino, 1993). Studies in experimental animals have shown that water applied to different regions of the pharyngeal mucosa is a more effective stimulus than pressure in terms of inducing pharyngeal swallowing (Storey, 1968). Neurons within the nucleus tractus solitariuus (NTS) of the brainstem swallowing neural network are multimodal, that is, they are excited by multiple sensory modalities (e.g., mechanical, gustatory, thermal). Thus, multi-modal stimuli are expected to facilitate swallowing more effectively than uni-modal stimuli.

Pharyngeal swallowing is also evoked in experimental animals by oropharyngeal and/or laryngeal application of: sodium chloride (NaCl), sodium sulphate ($Na_2SO_4$) sucrose, acetic acid, quinine-hydrochloride, and ethanol (Shingai and Shimada, 1976). A sour bolus (i.e., 50% lemon juice, 50% barium) has been reported to reduce swallowing latency in dysphagic patients following stroke, and reduce aspiration in patients with other etiologies of neurologically-based dysphagia (Logemann et al. 1995).

Figure 15:
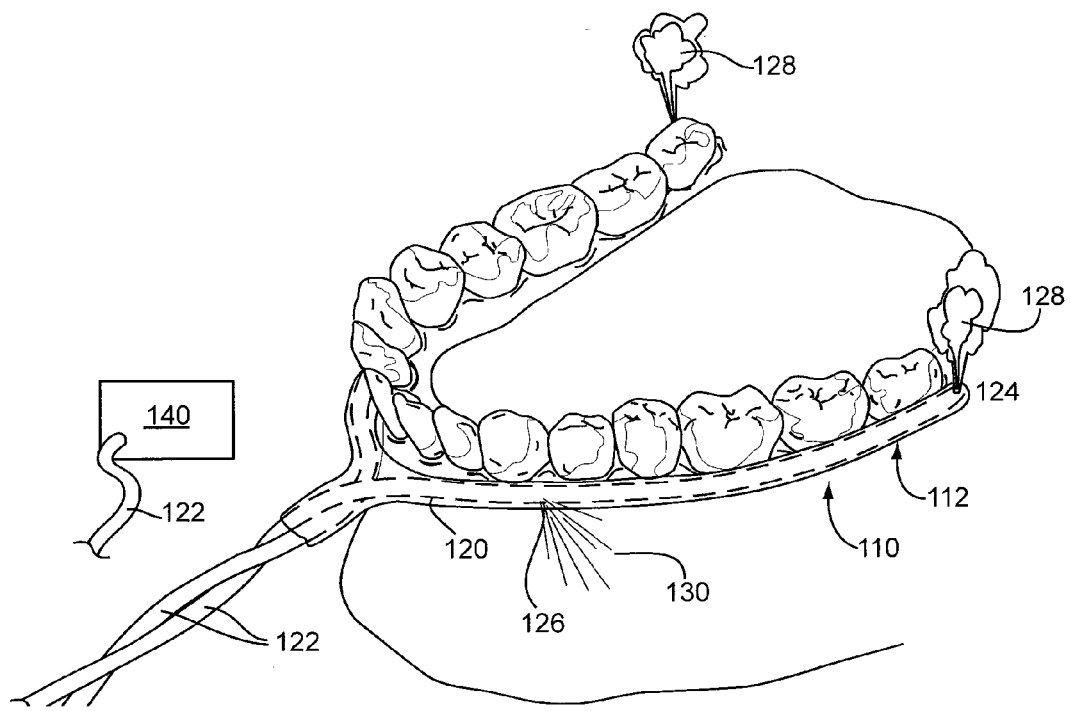
FIG. 15 is a perspective view of the mouthpiece shown positioned in a subject's vestibule and showing multiple ports.
Figure 31:
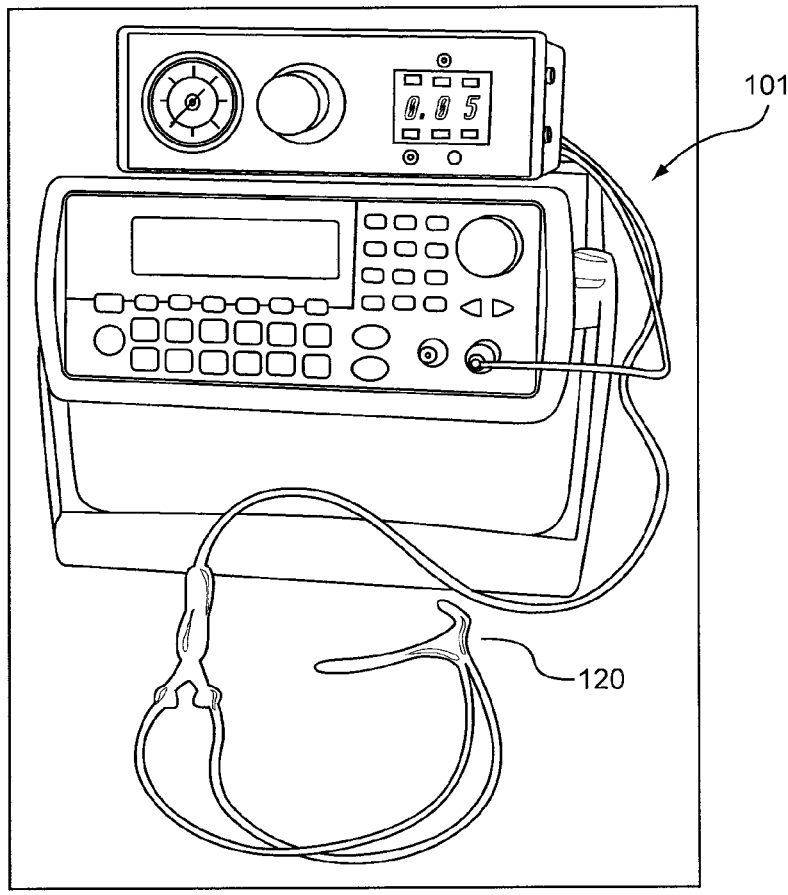
FIG. 31 shows the SWAPT system with attached mouthpiece for oropharyngeal application.

One embodiment of the Swallowing Air-Pulse Therapy with Aerosolized Liquid (SWAPT-AL) system is shown in FIG. 15. The aerosol delivery is regulated by a general control unit 140 (FIGS. 15 and 31). In one preferred embodiment, the components of the control unit may include a reservoir syringe that acts as a holding chamber for a liquid and a cap that articulates with the proximal end of the syringe. The cap houses tubing that provides a portal through which air pressure acts on the liquid. The SWAPT includes a catheter with one or more than one lumens. One lumen carries pressurized liquid. A second lumen carries pressurized medical air or a biocompatible gas. The catheter may involve one-or-more lumens ejecting air at its distal tip to aerosolize liquid that is simultaneously ejected from one-or-more lumens at its tip and in close proximity to the exit of the air-carrying lumens. An air-pressure regulator controls the (1) pressure acting on the liquid and gas (lumens) within the catheter, and (2) the duration of a single air pulse. A signal generator controls the duration of a train of air-pulses, and the frequency of pulses within the train. A pressurized tank supplies medical air and an associated air-pressure regulator. The liquid reservoir may include any sealed vessel or tube with at least one outlet that may be pressurized by pneumatic, hydraulic or mechanical means. The reservoir may be pre-filled upon manufacture, or be fitted with a port or opening to facilitate filling by the caregiver or user.

Using the SWAPT system shown in FIG. 31, studies were conducted to determine optimal parameters of oropharyngeal air-pulse trains in terms of eliciting saliva swallowing in healthy controls, with examination of (a) air pulse train duration, (b) pulse duration, (c) pulse frequency, and (d) pulse pressure. In one study, the system was driven by a portable nebulizer-type air compressor, while in another study the system was driven by compressed medical air from a pressurized tank (i.e., output pressure maintained at 40 psi). These studies showed that mean saliva swallowing rate increased with increases in air-pulse stimulation frequency between 2 and 12 Hz, with a Valvemate regulator upper frequency limited to 12 Hz. Frequencies of greater than 12 Hz, for example frequencies up to at least 80 Hz, may have even greater facilitatory effects on swallowing. Air-pulse train amplitude and duration had more variable effects on swallowing across subjects.

In an alternate embodiment the catheter may consist of a single lumen connected to a liquid reservoir. The lumen may be fitted with a nozzle at the distal tip to produce a spray upon expulsion of the reservoir contents. Or alternatively, the lumen may be of a sufficiently small diameter at the distal tip to produce a spray of liquid upon expulsion of the reservoir contents.

In a second alternate embodiment, small quantities of pressurized gas and liquid may be sequentially injected into a single lumen catheter via separate tubes or channels expending from the gas source and liquid reservoir to entry points located above the distal tip of the catheter shaft, and preferably near the proximal end. The catheter is sealed at the proximal end, and open at the distal tip. Upon actuation or triggering, a small bolus of liquid is first injected into the catheter. The channel to the liquid reservoir is then closed by a valve or similar means to prevent backflow of the liquid into the reservoir. Next, a small bolus of pressurized gas is injected at, or proximal to the point at which the liquid was injected. The pressurized gas serves to force the liquid out the catheter tip. The expansion of the pressurized gas upon expulsion assists in the aerosolization of the liquid. To further assist in aerosolization, the lumen can be fitted with a tapered nozzle at the distal tip to produce a spray upon expulsion of the liquid bolus. Or alternatively, the lumen may be of a sufficiently small diameter at the distal tip to produce a spray of liquid upon expulsion of the reservoir contents. Metering valves positioned on each of the channels connecting the gas source and liquid reservoir to the catheter can be used to dispense fixed quantities of compressed gas and liquid into the catheter upon each actuation. The reservoir valves may be manually, mechanically, pneumatically, hydraulically or electrically actuated at the desired rate of stimulation.

In a third alternate embodiment, the catheter may consist of more than one distal tip, thus providing a means of delivering aerosol simultaneously to multiple sites of the oral cavity, oropharynx, and pharynx. The aerosol may, thus, be delivered to receptive fields of the glossopharyngeal nerve and SLN, as well as the trigeminal nerve, the latter through a distal port positioned within the oral cavity of a person.

In yet another embodiment, the reservoir may contain a self-pressurized aerosol formulation consisting of a liquid and a compressed propellant gas such as those commonly used in spray cans or pharmaceutical metered dose inhalers. The reservoir may incorporate a metering valve to dispense a fixed quantity of propellant and liquid into the catheter upon each actuation. The reservoir valve may be manually, mechanically, pneumatically, hydraulically or electrically actuated at the desired rate of stimulation.

The gas pulse or aerosol pulse train or stimulus is directed to a region of the oral cavity, oropharynx, and/or pharynx by way of a mouthpiece within which the catheter is housed. In one embodiment, the distal tip of the catheter is positioned at the molar end of the mouthpiece. In an alternate embodiment, the output port through which the aerosolized liquid is ejected is positioned at another predetermined site within the oral cavity or oropharynx by virtue of the design of the mouthpiece. The mouthpiece may have a plurality of output ports within the oral cavity and oropharynx. This embodiment allows, for example, air pulses to be delivered to the oropharynx whilst aerosolized liquid pulses are delivered to a predetermined site within the oral cavity. Thus, the air pulses are directed toward receptive fields of IX and SLN that are known to play a role in pharyngeal swallowing initiation, while the gustatory (taste) stimului are directed toward receptive fields of the VII and IX nerves that are also involved in taste sensation.

In one SWAPT embodiment, the stimulus may be medical air. In the SWAPT-AL, the stimulus may be aerosolized liquid. In one embodiment, the aerosolized liquid stimuli are delivered within the following ranges:

Pulse Frequency: 1 Hz to 80 Hz
Single Pulse duration: 20 ms to 100 ms
Pulse train duration: 0.1 sec to 20 sec
Pulse Pressure: negative (−) 80 mm Hg to positive 240 mmHg (recorded at the distal (molar) end of the mouth piece). Sub-atmospheric pressure SWAPT generates suction at the point of delivery wherein fluid can be suctioned from the oral cavity.

In one embodiment, the aerosolized liquid is room temperature distilled water, or cold distilled water. In alternate embodiments of the invention, the aerosolized liquid contains one of the following: NaCl, sucrose, quinine, or lemon juice. Each of these liquids is employed at room temperature, or cold.

In addition to the advantage of providing multi-modal sensory stimulation, SWAPT with aerosolized liquid provides other benefits. For example, Dysphagia can result from a lack of saliva, that is, xerostomia. Xerostomia and associated swallowing impairment occurs in a number of patient diagnostic groups including persons who have undergone radiation therapy in the region of the salivary glands for treatment of cancer of the head or neck, persons with certain systemic conditions (e.g., Sjogren's syndrome), and persons taking medications that reduce salivary flow. In patients with dysphagia following radiation therapy, there is evidence that patients perceive their mouths to be even dryer than objective measures of saliva indicate (Logemann). Furthermore, the severity of dysphagia is correlated with the degree of perceived mouth dryness (Logemann). Thus, both dry mouth and the perception of dry mouth are problems for patients who have undergone radiation therapy of the head and neck. In addition to the association between dry mouth and dysphagia, dry mouth is unpleasant for the patient, reducing quality of life. By delivering aerosolized liquid to the oral cavity, oropharynx, and pharynx, SWAPT with aerosolized liquid provides a method and device for lubricating the oral cavity, oropharynx, and pharynx in patients with dry mouth. In this way, enhanced lubrication may (1) facilitate swallowing, and (2) moisten the upper airway, thus reducing the unpleasant sensation of dry mouth. Because the volumes of liquid are very small in the aerosolized form of SWAPT, the patient is not put at risk of aspiration as would be the case in a dysphagic patient swallowing larger volumes of liquid.

Clinical studies of SWAPT conducted in healthy controls and patients have provided evidence that modifications to an oral splint might provide advantages in terms of efficacy and patient comfort of SWAPT. In particular, patient feedback suggests that patients felt that a mouthpiece that fits over the lower teeth inhibited their swallowing, that is, the air-pulse evoked an urge to swallow but the mouthpiece then made it difficult to swallow. Participants indicated that any material between the upper and lower teeth inhibited swallowing, that is, made it more difficult to swallow. This was the case even when the material was very thin, for example 1 to 2 mm in thickness, which would be close to the just-noticeable difference for jaw opening of 1 mm.

Figure 17:
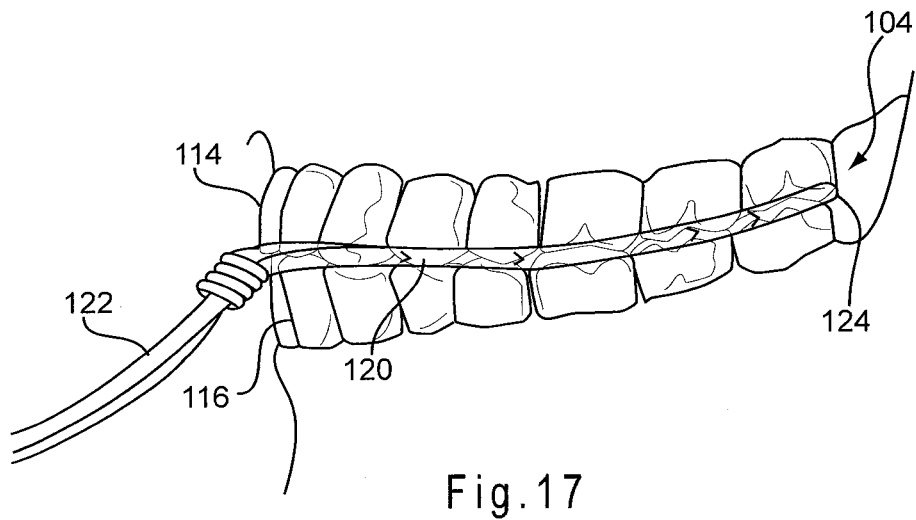
FIG. 17 is a perspective view of the mouthpiece shown positioned at the occlusal plane.
Figure 18:
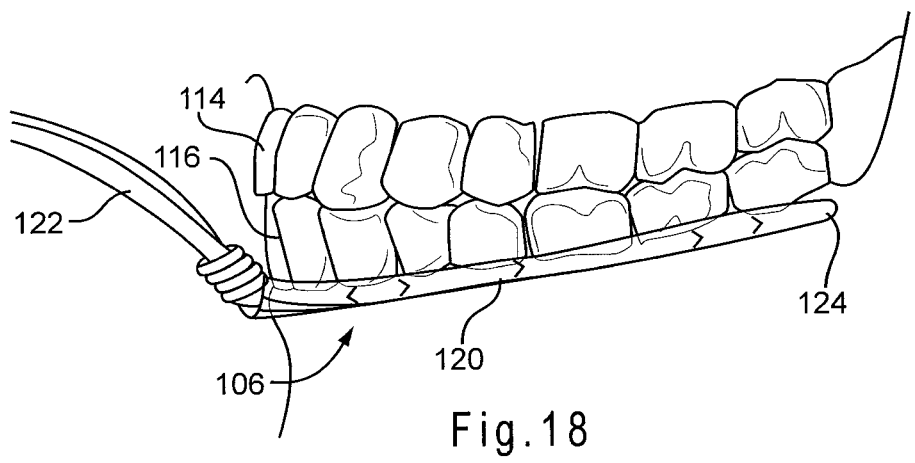
FIG. 18 is a perspective view of the mouthpiece shown positioned at the gingival margin of the lower teeth.

As used in this application, the term "oral appliance" includes an oral device, an oral splint, an oral cannula, an oral applicator, a buccal mouthpiece, a buccal appliance, a buccal cannula and/or a mouthpiece. The oral appliance directs stimuli to regions of the oral cavity, oropharynx, or pharynx, of a subject. In one embodiment, a SWAPT mouthpiece 100 sits within the vestibule 110, between the gingival surface of the alveolar bone and the cheek. The mouthpiece extends from the molar region 112 on one side of the mouth to the opposite molar region (see FIGS. 11 and 15). In this embodiment, there is no mouthpiece material between the upper and lower teeth 114, 116 (FIGS. 16-18).

Figure 16:
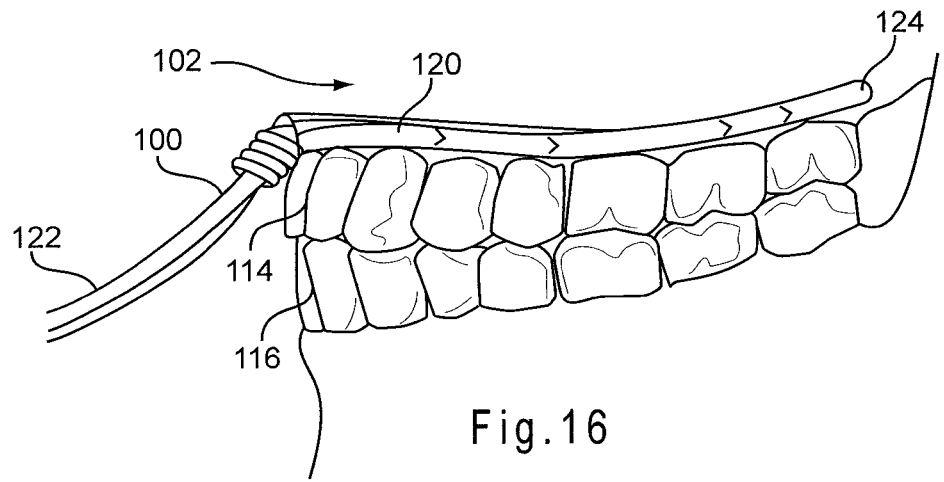
FIG. 16 is a perspective view of the mouthpiece shown positioned at the gingival margin of the upper teeth.

In one embodiment, shown in FIG. 16, the mouthpiece 100 sits within the upper vestibule 102. In another embodiment, shown in FIG. 18, the mouthpiece 100 sits within the lower vestibule 106. In yet another embodiment of the device, shown in FIG. 17, the mouthpiece 100 sits adjacent to the occlusal plane 104 of the upper and lower teeth 114, 116, within the vestibule. In one embodiment, the mouthpiece is between 5 mm and 20 mm high, and between 1 mm and 4 mm thick. The length of the mouthpiece, from right molar region to left molar region ranges from 3 cm to 20 cm. In one embodiment of the mouthpiece, the mouthpiece is trimmable, meaning it may be trimmed in length for optimal placement and fit. In edentulous patients, the mouthpiece fits between the upper alveolar margin and the cheek, or the lower alveolar margin and the cheek.

In one embodiment, the mouthpiece 100 is maintained in position by a stabilizing piece that fits around the lateral surface of the rear-most teeth as shown for example in FIG. 10. In one embodiment, as shown in FIGS. 14-18, the mouthpiece is made of dental resin 120. For example, the dental resin (i.e., STA-Vac sheet resin bleaching tray material #62851, 5" by 5", 0.040 soft EVA; Buffulo Dental Canada, Division of Bolton Dental Manufacturing Inc., Cambridge Ontario N3C 1Z1) is vacuum formed over an upper Dentoform (a mock-up of the upper dentition and alveolar structures). One or more lengths of fine-bore polyethylene tubing 122 (inner diameter: 0.045"; outer diameter: 0.062") are attached to the molded resin 120 along the margin between the teeth and the gingival margin. In one embodiment, one length of tubing extends on the right side of the dental form, and the other along the left side of the dental form by means of a knotted thread. Alternatively, larger bore polyethylene tubing is attached to the molded resin for the purpose of creating a conduit through which the aerosol catheter can be advanced within the mouthpiece in order to deliver aerosolized liquid. A malleable wire may also be attached to the molded resin. The wire permits contouring, if necessary, of the distal orientation of the outlet 124 of the catheter and provides a continuity that resists damage, such as biting by a person and thus releasing a piece of material that could be swallowed. A second layer of bleaching tray material is vacuum formed over the first layer, thereby enclosing the polyethylene tubing between the two sheets of dental resin. The bleaching tray material may be trimmed extensively, resulting in a small, flexible mouthpiece with tubing that exits posteriorly immediately posterior to the posterior-most tooth. Anteriorly, the tubing from the right and left sides exits the mouthpiece at the midline, passes between the subject's lips, and extends approximately 25 cm anterior to the lips where it connects securely with larger bore tubing at a Luer lock, or with another connector.

In yet another embodiment, the mouthpiece is made of dental impression material. A narrow sheet of dental wax (approximate length/height/thickness: 170 mm, 13 mm, 4 mm) is formed around an upper Dentoform (a mock-up of the upper dentition and alveolar structures; width at molar region: 54 mm). The wax is then removed from the Dentoform, while maintaining its contour. An impression of the wax is then made with dental impression material (3M ESPE Express FTD Vinyl Polysiloxane Impression Material Putty, 3M ESPE Dental Products, St. Paul, Minn. 55144-1000), effectively creating an impression tray (i.e., a trough) that approximates the shape of the wax that surrounded the upper dentition. A second, lighter weight dental impression material (i.e., Affinity Hydroactive Impression Material, Vinyl Polysiloxane, heavy body, regular flow, regular set; Clinician's Choice Dental Products Inc., 1980 Hyde Park Rd., London N6H 5L9) is then injected into the impression trough until the level of impression material-occupies half the height of the impression trough. One or more lengths of fine-bore polyethylene tubing (inner diameter: 0.045 inches; outer diameter: 0.062 inches) are set within the right and left sides of the impression tray, respectively. Alternatively, larger bore polyethylene tubing is set within the impression tray for the purpose of creating a conduit through which the aerosol catheter can be advanced within the mouthpiece in order to deliver aerosolized liquid. The double tubing can also be extruded as a single piece, such that they can be separated by force or by pulling to create the two separate sections to go into the mouthpiece. A malleable wire may also be set within the impression tray. The wire permits contouring, if necessary, of the distal orientation of the outlet of the catheter and provides a continuity that resists damage, such as biting by a person and thus releasing a piece of material that could be swallowed. The tubing exits the impression trough anteriorly and posteriorly through small-bore openings that are placed in the impression material. Additional impression material is then injected into the trough, over the tubing, such that the tubing is fully surrounded by impression material within the right and left sides of the impression trough. The dental impression material is trimmed, resulting in a small, flexible mouthpiece that fits within the vestibule between a patient's upper teeth and the cheek and houses the polyethylene tubing. The polyethylene tubing exits the dental impression material posteriorly, on the right and left sides, immediately posterior to the posterior-most tooth, and terminates flush with the impression material. The tubing from the right and left sides exits the mouthpiece anteriorly in the region of the upper central incisor teeth where it passes between the patient's lips and extends approximately 25 cm anterior to the lips where it connects securely with larger bore tubing at a Luer lock, or with another connector.

In yet another embodiment, the mouthpiece is made of high-temperature-heat-resistant silicone with a nylon core. The silicone is molded in a method similar to that described above for the dental impression material mouthpiece. The heat resistant silicone with nylon core provides a mouthpiece that can be sterilized and, thus, employed repeatedly by a patient.

The various mouthpiece embodiments may have a plurality of output ports 124, 126 as shown in FIG. 15, which are located within the oral cavity and oropharynx. This embodiment allows, for example, air pulses 128 to be delivered to the oropharynx whilst aerosolized liquid pulses 130 are delivered to a predetermined site within the oral cavity. Thus, the air pulses 128 are directed toward receptive fields of IX and SLN that are known to play a role in pharyngeal swallowing initiation, while the gustatory (taste) stimuli are directed toward receptive fields of the VII and IX nerves that are involved in taste sensation.

In various embodiments, the polyethylene tubing 122 exits the mouth at an angle, as shown in FIGS. 16-18. In one embodiment, the tubing exits the mouthpiece along the same-horizontal plane as the mouthpiece. This design is optimal when the mouthpiece is positioned along the subject's occlusal plane. In an alternate embodiment of the mouthpiece, the tubing exiting the oral form is contoured such that, immediately after exiting the oral form 120, it follows approximately an 80 degree angle. The tubing then exits the patient's mouth, running between the upper and lower lips. This angle of the exiting tubing is optimal when the mouthpiece is positioned within the vestibule 102 along the buccal surface of the upper teeth, or the vestibule 106 along the buccal surface of the lower teeth. The angle of the tubing ensures that the mouthpiece stays in position along the buccal surface of the upper or lower teeth, or, in edentulous patients, along the upper or lower alveolar margin. Another advantage of this design is that the mouthpiece can be positioned either along the upper or lower teeth, or upper or lower alveolar margin. That is, a single mouthpiece can be used for both the upper dental arch, or lower dental arch, positions, by orienting the tubing inferiorly, or superiorly, respectively as shown in FIGS. 16 and 18. This has advantages for patients with anatomic abnormalities of either the upper or lower teeth/alveolar margin, for example, as a result of surgery and reconstruction for treatment of oral cancer. The patient can position the mouthpiece along the intact dental arch.

In another embodiment, the mouthpiece 100 is coated with an oral antiseptic to provide a means of enhancing oral hygiene in the user. This is advantageous since poor oral hygiene has been shown to be a strong predictor of aspiration pneumonia among institutionalized patients. The causal link between poor oral hygiene and aspiration pneumonia appears to be aspiration of contaminated oral secretions. This is a particular problem among persons with swallowing impairment in which aspiration is a frequent feature of the swallowing pattern. Therefore, it may be advantageous for the SWAPT mouthpiece to be coated with an oral antiseptic such that use of the device would enhance oral hygiene, in addition to facilitating swallowing.

The various mouthpiece embodiments provide several advantages. For example and without limitation, the patient is able to maintain his/her upper and lower teeth 114, 116 in occlusion. This is preferable since kinematic studies of swallowing have shown that the upper and lower teeth are positioned along or near the occlusal plane 104 during the pharyngeal stage of swallowing. Thus, the upper and lower teeth may be in occlusion whilst the device is "in situ" in the subject's mouth, occlusion being the preferred posture of the jaw/teeth during swallowing. The mouthpiece 100 also has a relatively small impact on the resting position of the subject's mouth, tongue, oropharynx, and face. For example, the tongue in rest position does not make contact with the mouthpiece. Because the mouthpiece is thin, the subject is able to achieve closure of the lips. The mouthpiece 100 also does not come in contact with pooled saliva in the sublingual region or along the lingual surfaces of the teeth. Being positioned within the upper or lower vestibule 102, 104, the subject/patient can ingest and swallow liquid or solid bolus with the mouthpiece in situ. Thus, the mouthpiece may be inserted into the vestibule with the mouthpiece having a small channel sufficient to allow enough gas or aerosolized liquid to pass to facilitate swallowing and potentially allow the patient to intake and masticate food and drink while the mouthpiece is in place.

In one embodiment, the mouthpiece is constructed out of a material(s) (single or multi lumen) that would prevent the patient from fragmenting (biting) the mouthpiece. For example, heat resistant silicone is sufficiently strong to prevent a person from fragmenting the mouthpiece. The use of a malleable wire within the mouthpiece also permits contouring, if necessary, of the distal orientation of the outlet of the catheter and also provide a continuity that is resistant to being bitten through and so releasing a piece of material that could be swallowed. The mouthpiece is constructed in such a way as to also prevent swallowing (partially) or gagging on the mouthpiece.

As discussed above, neurons within the NTS are multi-modal, that is, they are excited by multiple sensory modalities (e.g., mechanical, gustatory, thermal). Thus, multi-modal stimuli are expected to facilitate swallowing more effectively than uni-modal stimuli. Furthermore, pharyngeal swallowing is also evoked in experimental animals by oropharyngeal and/or laryngeal application of: sodium chloride (NaCl), sodium sulphate ($Na_2SO_4$), sucrose, acetic acid, quinine-hydrochloride, and ethanol. A sour bolus (i.e., 50% lemon juice, 50% barium) has been reported to reduce swallowing latency in dysphagic patients following stroke, and reduce aspiration in patients with other etiologies of neurogenic dysphagia.

As described above, one method provided to deliver multi-modal sensory stimuli that include a gustatory component for swallowing facilitation is through the use of aerosolized SWAPT, for example through port 126. In various embodiments, the aerosolized liquid 130 contains one of the following: NaCl, sucrose, quinine, or lemon juice. Each of these liquids is employed at room temperature, or cold.

Another alternate method for delivering multi-modal stimuli that include a gustatory component is by applying a gustatory stimulus to the SWAPT mouthpiece 100. Thus, what is claimed is a flavour-treated mouthpiece. The gustatory stimulus is provided as a manufactured aspect of the mouthpiece in the form of a coating or impregnation of the gustatory stimulus that provides a means for the gustatory stimulus to be released in the subject's oral cavity when the material elutes over a period of time as it comes in contact with, and is moisturized by, the subject's oral saliva and oral secretions. In this way, a gustatory stimulus is supplied by the mouthpiece while the mechanical and thermal stimulus components are supplied in the delivered air-pulse trains or aerosol-pulse trains. Thus, the mouthpiece is impregnated with a flavour ingredient that elutes over a period of time when moisturized after insertion into the vestibule or mouth.

A cool percept associated with the SWAPT air-pulse trains may reflect at least three mechanisms: (1) the use of room-temperature air providing a stimulus that is cooler that the subject's intra-oral temperature, (2) the expansion of the compressed SWAPT air as it exits the tubing within the mouthpiece that may reduce the air temperature, and (3) the evaporation of liquid within the mouth by the air-pulse train, that is, the evaporation of saliva, which may contribute to the perception of a cool stimulus within the oral cavity or oropharynx. These thermal properties of SWAPT are seen as an advantage over other technologies that utilize an external cooling control system to cool the gas or other oral stimulus before it enters the subject's mouth. External cooling systems for delivery of temperature-controlled stimuli within the mouth may be problematic because of the distance that must be traversed between the site of cooling, and the desired site of stimulation within the oral cavity or oropharynx. In contrast, the mechanisms that are believed to underlie the thermal property of SWAPT operate within the subject's oral cavity and oropharynx, precluding the need for an external cooling control system. Thus, a thermal stimulus is provided to the oral cavity and oropharynx wherein the thermal property is provided through the inherent properties of the stimulus and the stimulus delivery system, both being located fully within the oral cavity or oropharynx of a person.

Figure 19:
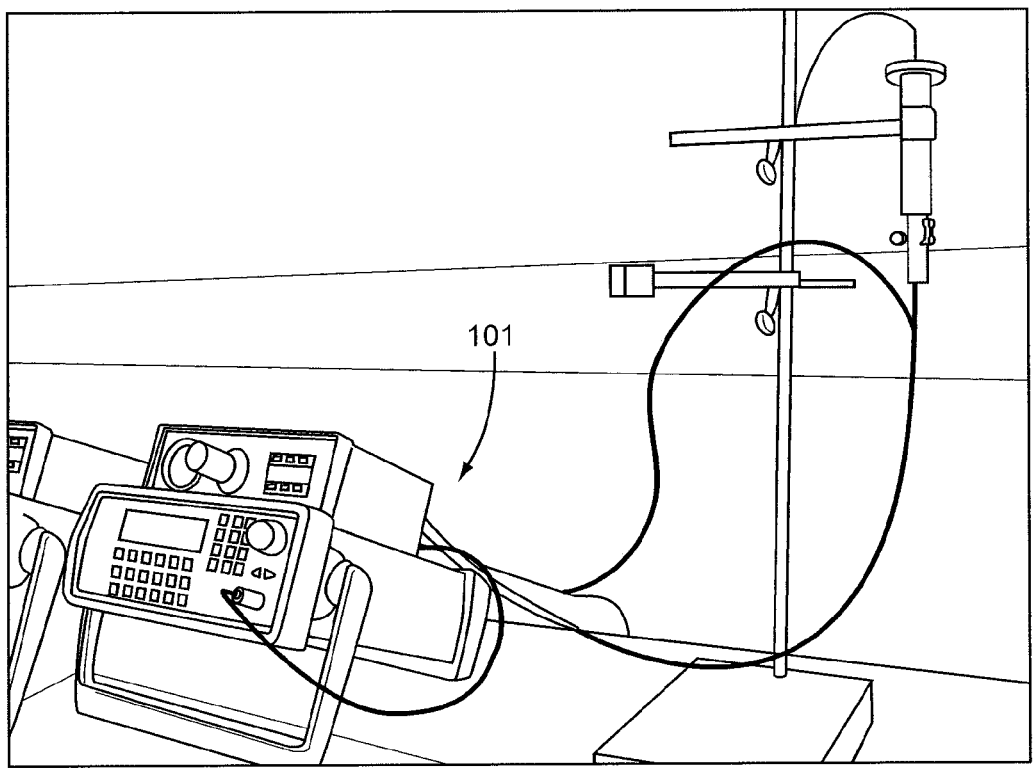
FIG. 19 is an illustration of the swallowing air pulse system including a signal generator, air pressure regulator, mouth piece and system for delivering a substance.

In an alternate embodiment, the temperature of the gas 128 or aerosolized liquid stimulus 130 used in SWAPT, and SWAPT-AI, respectively, is altered by means of a control system that is external to the oral cavity. The control unit 140 may be positioned and set to apply a sensory stimulus to the oral cavity or oropharynx or pharynx at some predetermined time. This predetermined time point may be defined in relation to (1) time, (2) in advance of, or simultaneous with, an attempt to perform a swallow, or another behaviour performed by a person (e.g., patient or clinician), or (3) a physiologic event in a person, as determined from the output of a transducer positioned on the person, oral or oropharyngeal sensorimotor behaviour, by a person. The control system includes a signal generator and an air-pressure regulator 101, for example a Valvemate regulator, as shown in FIGS. 19 and 31.

In one group of embodiments, the onset and offset of the sensory stimulus (SWAPT or SWAPT-AL) may be triggered in a number of ways, including physiologic events in the patient, for example, respiratory-related movements associated with various phases of the respiratory cycle, laryngeal movement, or electromyographic activity (for example, recorded from surface electrodes placed over the suprahyoid musculature (i.e., under the chin) that are recorded from transducers positioned on the patient; the output signals are compared with a predetermined threshold and, if the signal exceeds the predetermined threshold, the SWAPT stimulus is delivered. The system may also be activated by a patient or clinician, for example, by a button press or an alternate manual means of triggering stimulus delivery; the patient or clinician could, thus, initiate SWAPT or SWAPT-AL in relation to bringing food/drink toward the mouth, or ingesting food, or swallowing food, or when the patients feels ready to swallow. A cue or instruction may also be provided to the patient as a conditioning stimulus (e.g., an auditory tone) or an instruction to the patient to initiate a behavior, for example, to commence swallowing or chewing. The system may also be activated on a temporal basis, for example, by triggering SWAPT or SWAPT-AL every several minutes when swallowing of accumulated saliva is desired by a patient. The system may also be activated on the basis of combinations of these various mechanisms. Thus, the onset of SWAPT or SWAPT-AL could be triggered as a function of time to occur every three minutes for the purpose of swallowing accumulated saliva; the offset of the SWAPT stimulus sequence would be triggered based on the occurrence of a swallow (determined from the laryngeal force sensor) in relation to SWAPT such that SWAPT air-pulse trains would continue until a swallow occurred, after which it would be terminated and subsequently, be applied again at 3-minute intervals.

Habituation, defined as the reduction of responsiveness to a stimulus after prolonged or repeated exposure to the stimulus, is a ubiquitous feature of neural processing. Habituation can be seen as an adaptive process whereby the nervous system ceases to respond to unimportant stimuli within an environment of multiple completing stimuli. Habituation has been demonstrated in human responses to auditory, visual, and somatic stimuli.

One embodiment of the SWAPT 100 provides a means of delivering a sequence of distinct air-pulse trains, or aerosol-pulse trains to the oral cavity, oropharynx, or pharynx of a person, where a train is defined as a series of at least one pulse. The individual air-pulse trains may vary in terms of the following pulse parameters: pulse duration, pulse amplitude, pulse frequency, and train duration. The air-pulse trains (of varying pulse parameters) are presented in random order within a predetermined sequence. By altering the stimulus characteristics of successive pulse trains, habituation to SWAPT or SWAPT-AL is expected to be reduced because the nature of the stimulus is variable as a function of time. Thus, the salience of the SWAPT stimuli is expected to be maintained over time to a greater degree than would be expected with a system in which a given sensory stimulus is repeatedly delivered to the patient/subject. In this way, the predetermined sequence of variable pulse trains optimizes the facilitatory effect of SWAPT.

Figure 21:
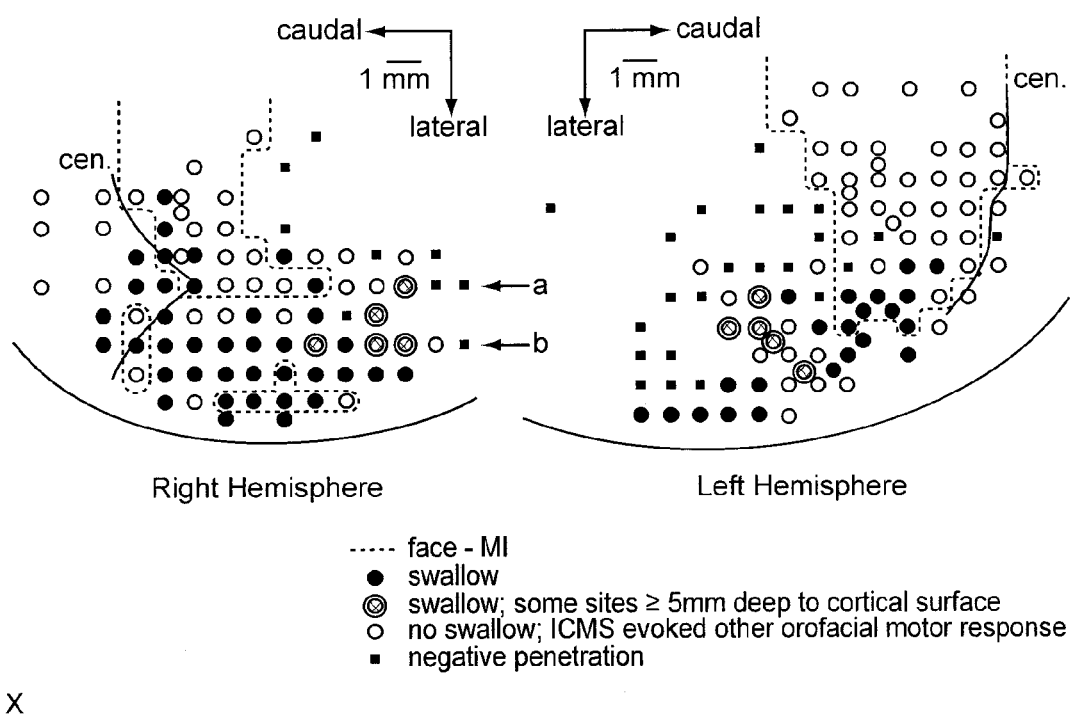
FIG. 21 shows an intracortical microstimulation of the lateral primary motor cortex showing face primary motor cortex.
Figure 22:
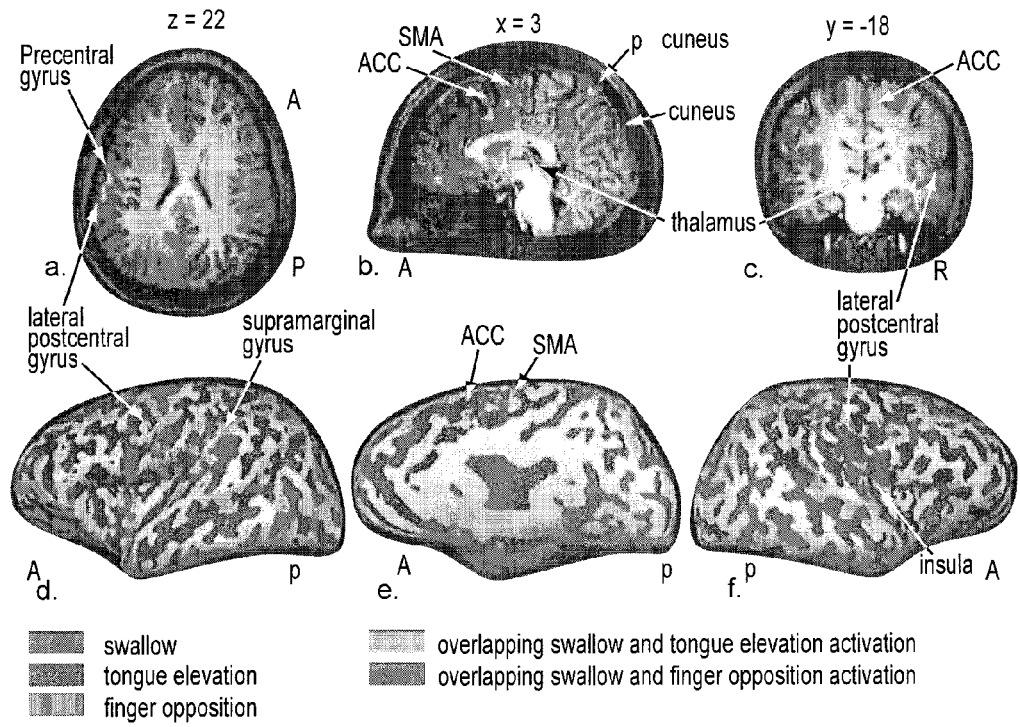
FIG. 22 shows functional magnetic resonance imaging of swallowing, tongue elevation, and finger opposition.

Previous electrophysiological studies in primates (Martin et al. 1993, 1995, 1997; Sessle et al. 2005), and NSERC- and HSF funded brain imaging studies in humans (Martin et al. 2001, 2004; Toogood et al., 2005, 2006), have shown that, in addition to known brainstem areas, swallowing is processed within a large-scale inter-hemispheric network of cortical foci. Many of these foci were localized to sensory and sensory association cortical regions (see FIGS. 21 and 22), underscoring the importance of sensory inputs in swallowing regulation. After comparing the effects on swallowing of several sensory stimuli, it was determined that air pulses were superior in terms of swallowing facilitation and clinical feasibility. SWAPT directs predetermined trains of discrete air pulses to the posterior aspect of the mouth and oropharynx, near the tonsil (FIG. 23) where receptive fields, innervated by the superior laryngeal nerve (SLN) and the pharyngeal branch of the glossopharyngeal nerve (GPNph), are believed to be "reflexogenic" for swallowing (Mu and Sanders, 2000; Yoshida et al., 2000).

Figure 24:
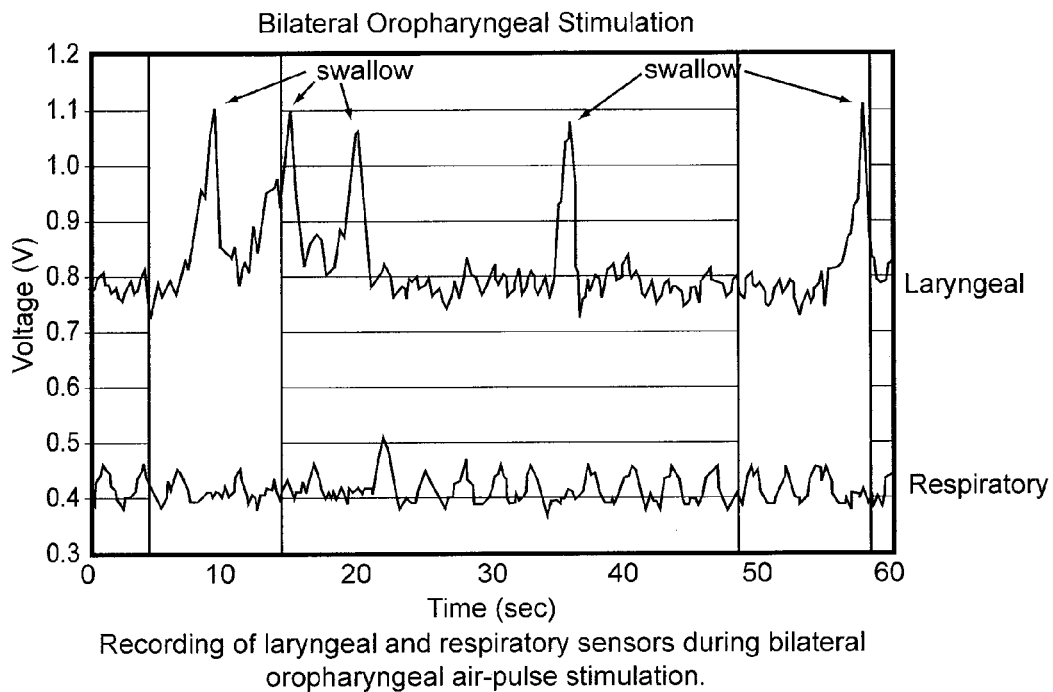
FIG. 24 shows recordings of laryngeal and respiratory sensors during bilateral oropharyngeal air-pulse application.
Figure 25:
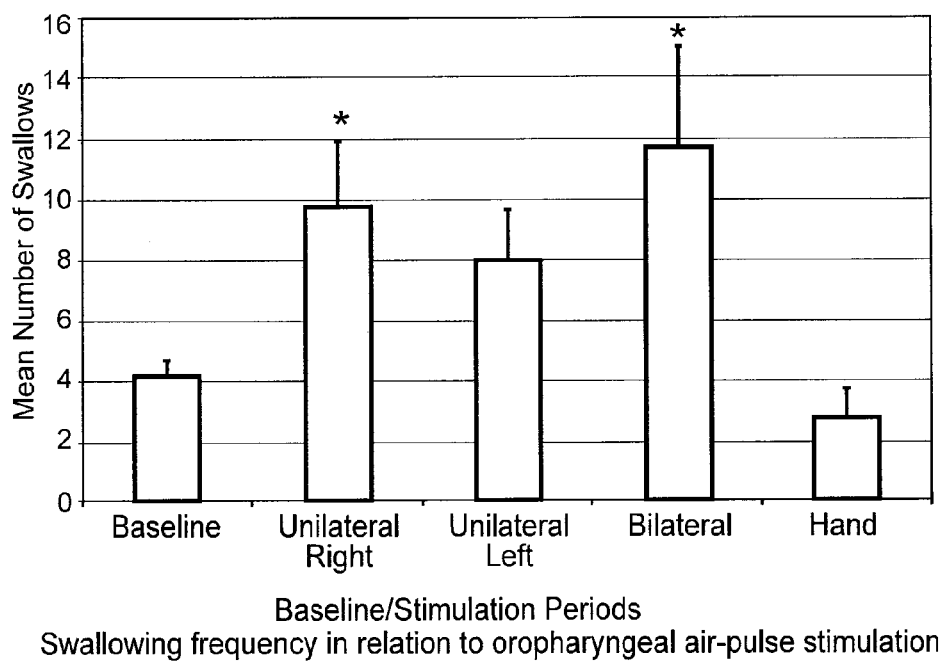
FIG. 25 shows swallowing frequency in relation to oropharyngeal air-pulse application.
Figure 26:
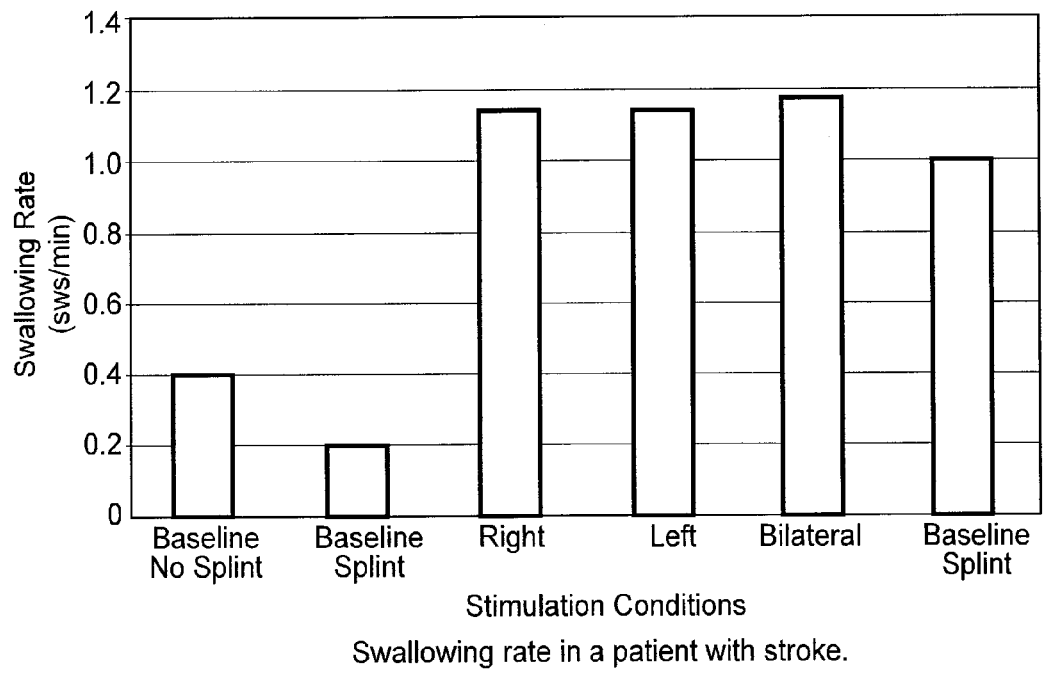
FIG. 26 shows swallowing rate in a patient with dysphagia.
Figure 27:
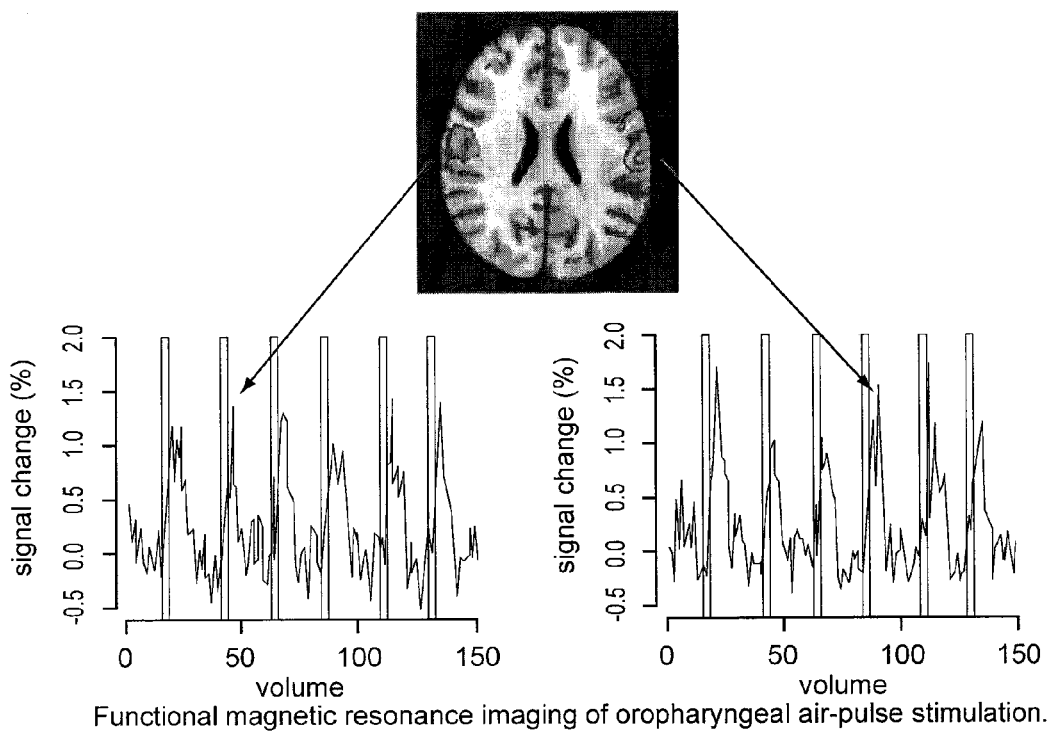
FIG. 27 shows functional magnetic resonance imaging of oropharyngeal air-pulse application.
Figure 28:
FIG. 28 shows functional magnetic resonance imaging of air-pulse induced associated swallowing.

Air-pulse stimulation applied to the peri-tonsillar region of the oropharynx in healthy controls evokes an irrepressible urge to swallow, followed by a frank swallow as verified by laryngeal and respiratory movement patterns (Therurer et al., 2005), as shown in FIG. 24. Moreover, air-pulse stimulation produces a significant increase in the frequency of saliva swallowing (FIGS. 24 and 25), with bilateral stimulation having a greater effect than unilateral. These findings were replicated and extended in to larger samples of healthy controls (N-16, Fortushnick et al; N=15, Girma et al.), and in a preliminary study of 2 patients with dysphagia secondary to stroke demonstrates such results as shown in FIG. 26 (Theurer et al. 2005b).

In parallel with various behavioral studies, high-field functional magnetic resonance imaging (fMRI) has been used to study the neural processing of oropharyngeal air-pulse application. For example, SWAPT activates a distributed brain network including the primary somatosensory cortex and the thalamus, classical motor areas (primary motor cortex, supplementary motor area, cingulated motor areas and basal ganglia) and polymodal regions (including the insula, inferior parietal cortex and frontal cortex) (Soros et al., 2008), as shown in FIG. 26. These cortical areas overlap regions previously implicated in oral and pharyngeal sensorimotor functions such as tongue movement, mastication, and swallowing. Swallows that are produced at short latency after air-pulse stimulation activate the same cortical network as habitual swallows, suggesting that air-pulse application might be used to "drive" the cortical swallowing network as shown in FIG. 26.

Figure 23:
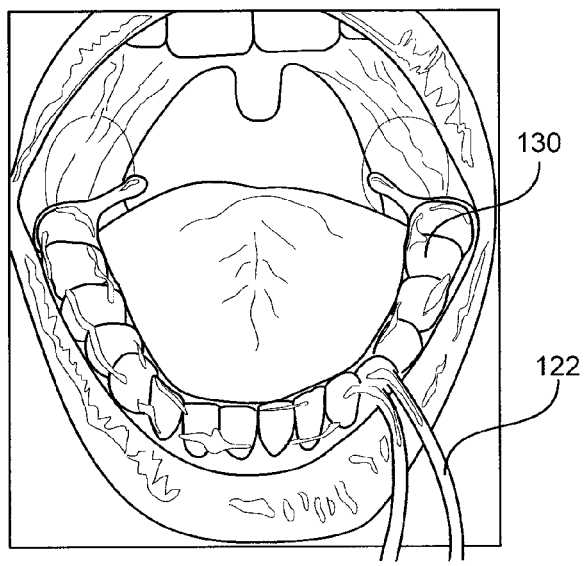
FIG. 23 shows a lower dental splint for the delivery of oropharyngeal air-pulse application.
Figure 29:
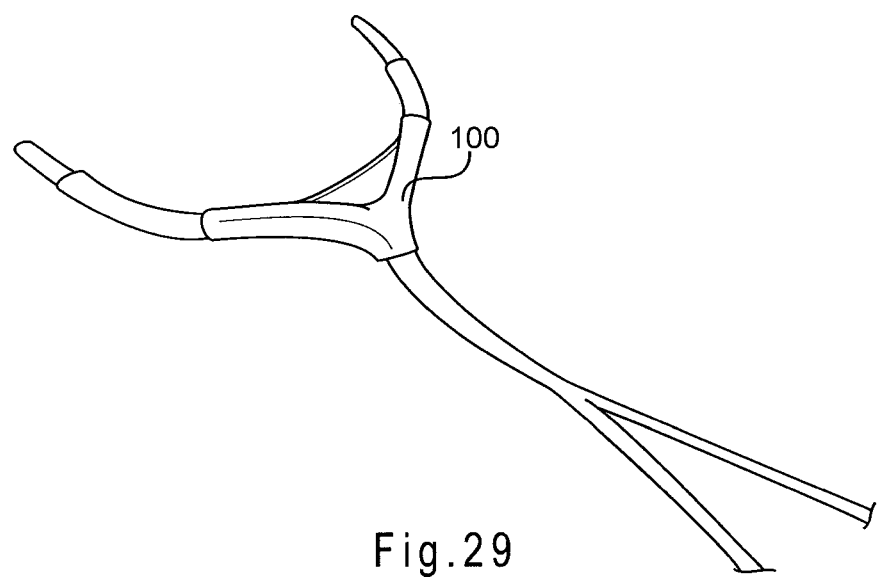
FIG. 29 shows a buccal mouthpiece for oropharyngeal air-pulse application.
Figure 30:
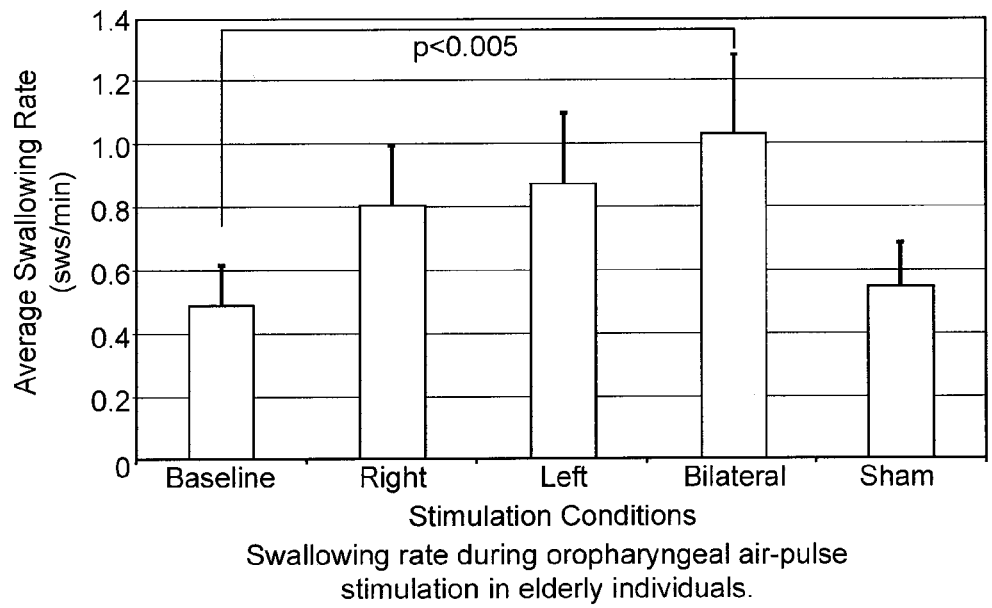
FIG. 30 shows swallowing rate during oropharyngeal air-pulse application in elderly individuals.

The SWAPT air pulse trains are delivered to the oropharynx via a mouthpiece 130 (see e.g., FIG. 23). One embodiment of the SWAPT mouthpiece 130 employed a custom silicone mouthpiece that fit over the lower dentition (FIG. 23). In another embodiment, the SWAPT mouthpiece 100 sits within the buccal cavity, between the teeth and cheek (FIG. 29). In this embodiment, there is no mouthpiece material between the upper and lower teeth based on patient feedback indicating that inter-dental material was perceived as inhibiting swallowing. The new mouthpiece is made of 1 mm thick dental resin (i.e., bleaching tray or mouth-guard material) that is vacuum-formed over a Dentoform (a mock-up of the dentition and alveolar structures). Two lengths of fine-bore polyethylene tubing (inner diameter: 0.045 inches; outer diameter: 0.062 inches) are attached to the molded resin along the Dentoform margin between the teeth and the gingiva, one on the right side of the dental form, and the other along the left side of the dental form. A second layer of resin is vacuum formed over the first layer, thereby enclosing the polyethylene tubing between the two sheets of dental resin. SWAPT efficacy with the mouthpiece of FIG. 29 was demonstrated in a sample of 18 healthy geriatric participants as shown in FIG. 30 (Theurer et al., 2008).

The buccal mouthpiece 100 has several advantages. The patient is able to maintain his/her upper and lower teeth 114, 116 in occlusion. This is preferable since kinematic studies of swallowing have shown that the upper and lower teeth are positioned along the occlusal plane during the pharyngeal stage of swallowing. The mouthpiece appears to have a relatively small impact on the resting position of the subject's mouth, tongue, oropharynx, and face. For example, the tongue in rest position does not make contact with the mouthpiece. Because the mouthpiece is thin, the subject is able to achieve closure of the lips. The mouthpiece does not come in contact with pooled saliva in the sublingual region or along the lingual surfaces of the teeth. Being positioned within the upper or lower buccal region, the mouthpiece potentially allows the patient to ingest and swallow food and drink while the mouthpiece is in place.

Figure 20:
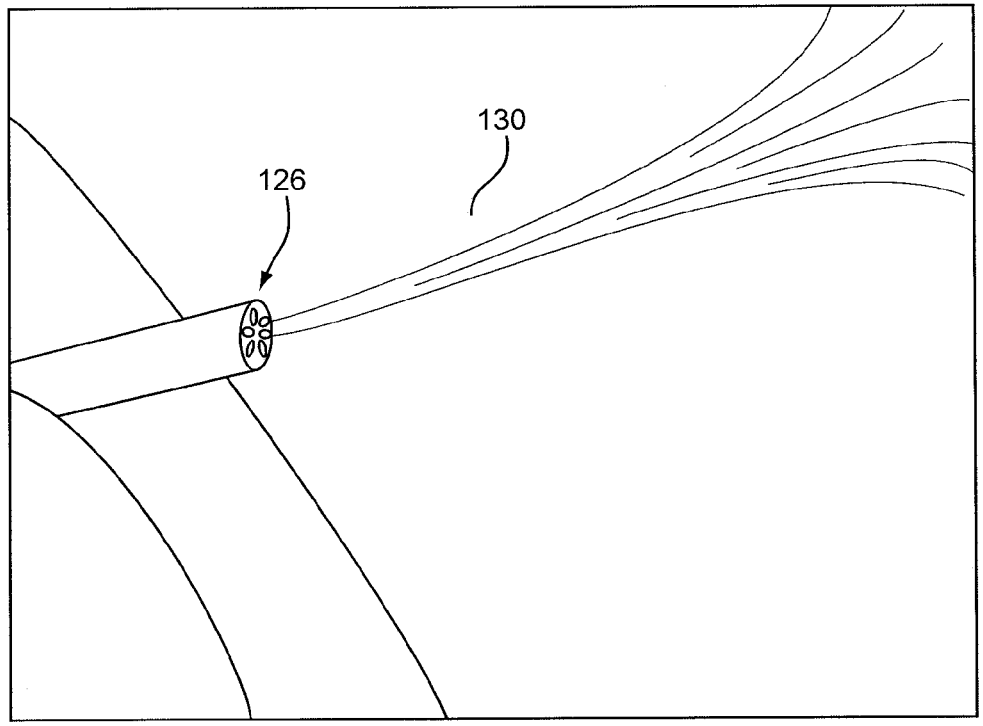
FIG. 20 is magnified illustration of an aerosol catheter with aerosolized liquid exiting the tip.

Referring to FIGS. 1-5, another embodiment of a mouthpiece, referred to as an oral cannula 2, for delivering a gas to the mouth of a user is shown. The oral cannula may include a pair of flexible tubes 4, 6 configured to be positioned on opposite sides of the face of a user. Of course, it should be understood that the oral cannula may include only a single tube disposed on one side of the user's face. The oral cannula may also be configured with two tubes, but with gas being delivered through only one of the tubes in some desired treatment modalities. The flexible tubes 4, 6 may be made of thermoformed tubing, which can be formed into a particular shape and configuration, but which has some flexibility and ability to conform to the face and mouth of the user. In one suitable embodiment, the flexible tube is made of polyurethane, polyethylene, PVC, other suitable and biocompatible materials, and/or combinations thereof. The tubes may have a $\frac{1}{8}^{th}$ inch outer diameter and a $\frac{1}{16}^{th}$ inch inner diameter forming a lumen. Of course, other size tubes may also be suitable, and the cross-sectional shape may be circular, or configured in other geometrical shapes. The tubes may be clear or transparent, translucent, coloured or opaque, and/or various combinations thereof, with the visual characteristics varying along the length of the tube for example so as to provide one or more windows. Each tube may also be formed with a plurality of lumens, or channels, to allow for additional features such as light, sensors, fluid delivery, etc., including for example and without limitation the delivery of an aerosolized liquid 130 through a port 126, shown for example in FIG. 20. In such embodiments, the lumens may run parallel to each other, and include for example and without limitation a first inner lumen and a second exterior lumen formed around the inner lumen, or alternatively two or more lumens running side by side. Of course, the plurality may include more than two lumens.

In one embodiment, shown in FIG. 13, a wire 8 runs along a length of at least a portion of the flexible tubing 4, 6. The wire provides further shape memory to the flexible tubing. The wire may be co-extruded with the tube, or may be connected to the tubing by molding, welding, adhesives and the like, or combinations thereof.

Referring to FIGS. 1-5, the flexible tube 4, 6 may be made of, impregnated with, or coated with a flavored material, including without limitation fruit (e.g., lemon), menthol or mint flavors, which may be pleasing to the user and which may facilitate swallowing. The tube may also be made of, impregnated with, or coated with, an antistatic material, or alternatively a conductive material. Antistatic materials have a surface resistivity of between about 10E10 ohm/sq and about 10E 12 ohm/sq. Static dissipative materials have a surface resistivity of between about 10E6 ohm/sq. and about 10E12 ohm/sq. Conductive materials have a surface resistivity of between about 10E1 ohm/sq and about 10E6 ohm/sq. Metals typically have a surface resistivity of between about 10E-1 to about 10E-5 ohm/sq. Surface resistivity as set forth herein is measured pursuant to ASTM test D257. The tubing may also be made of, or coated with, an antibacterial material. For example, silver impregnation may provide antibacterial properties.

Each flexible tube 4, 6 includes an inlet portion 10, which is preferably elongated and may extend from the neck region to the ear of the user. The inlet portion has an inlet end portion 12 connected to an adapter (e.g., Y adapter) 14, with the adapter having a feed tube 16 connected to an opposite end thereof. A slideable connector 20, configured in one embodiment as a sleeve, is disposed over and slidably receives the inlet portions 10 of the tubes. The connector 20 may be moved back and forth along a portion of the lengths of the inlet portions 10 of the tubes so as to lengthen the end portion 12, and thereby secure the tubes under the chin of the user, or to shorten the end portion 12, and thereby loosen the tubes for comfort or removal.

The feed tube 16 is configured to connect to a gas source 22, for example and without limitation by way of a quick connect 18 having a releasably component, such as a detent. The term "gas" refers to and includes air, oxygen, and/or any other type of gaseous substance suitable for breathing by humans, including for example and without limitation Heliox. The gas may also include various medicaments entrained therein for further treatment of the user, for example various medicaments applied via an aerosol such as antibiotics for pulmonary infections or COPD medications. The gas source is configured to emit pulses of gas, with the volume, temperature, pressure, duration and/or frequency being controlled by a central processor and control system. The gas source can alternatively be configured to emit a continuous source of gas. The system can also be configured to sense the respiratory cycle of the user, such that gas is delivered only during a certain portion of the cycle, e.g., during exhalation. Various exemplary control systems are shown and disclosed in US Pub. No. 2006/0282010A1, entitled Oral Device, the entire disclosure of which is hereby incorporated herein by reference.

Figure 5:
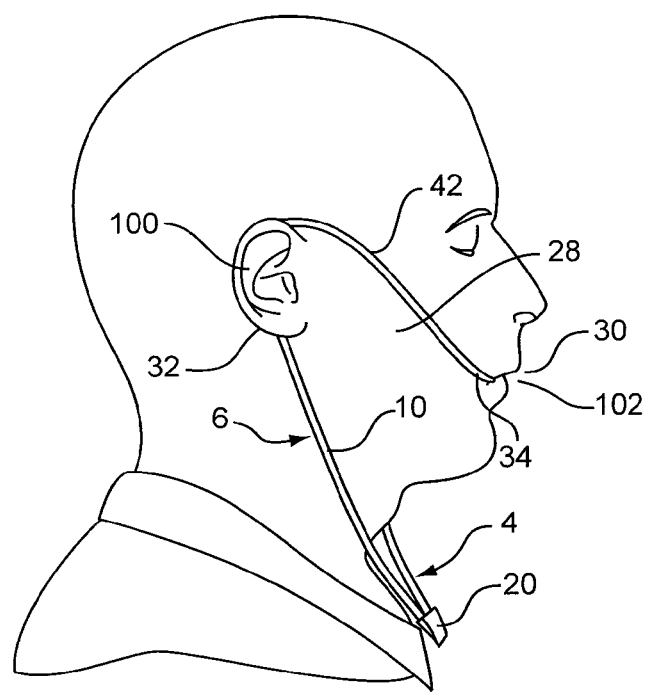
FIG. 5 is a side view of a user with the oral appliance of FIG. 1 located in an operational position.
Figure 6:
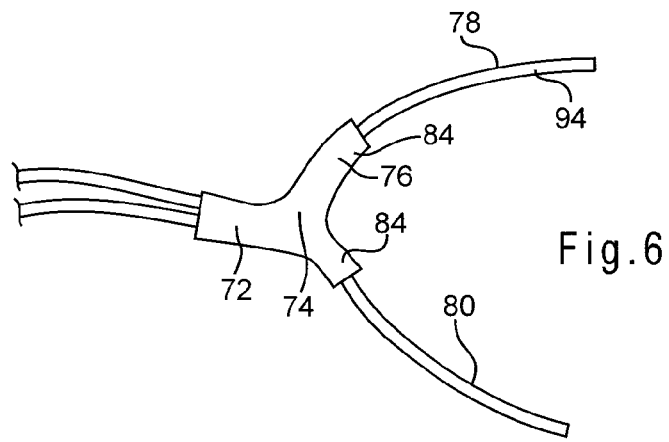
FIG. 6 is a perspective view of a second embodiment of an oral appliance.
Figure 7:
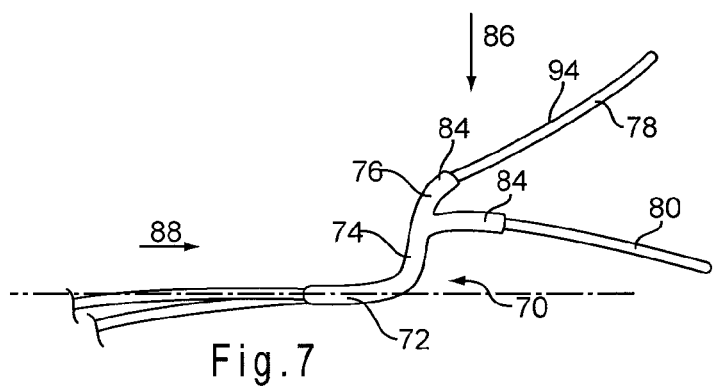
FIG. 7 is a side view of the oral appliance shown in FIG. 6.
Figure 8:
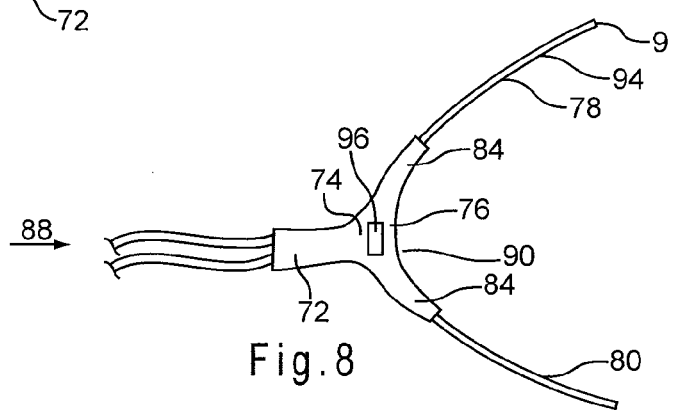
FIG. 8 is a plan view of the oral appliance shown in FIG. 6.
Figure 9:
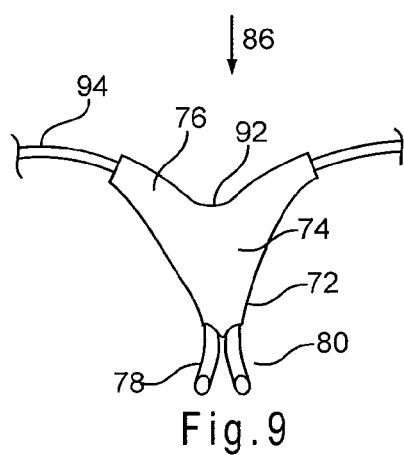
FIG. 9 is a front view of the oral appliance shown in FIG. 6.
Figure 14:
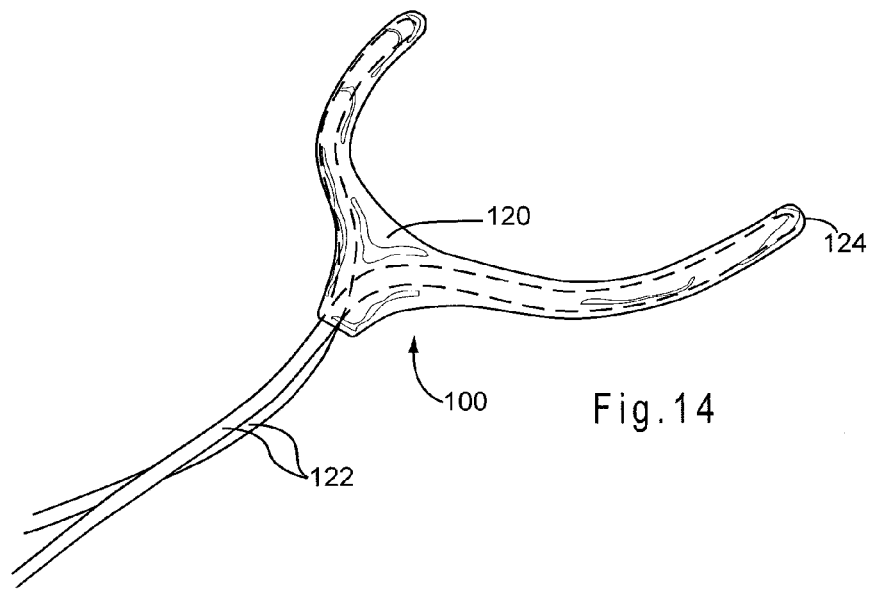
FIG. 14 is a perspective view of one embodiment of the mouthpiece.

Referring to FIGS. 1-5, the pair of tubes 4, 6 are a mirror image of each other, or can be folded one onto the other, along a longitudinal axis 24. As shown in FIGS. 1 and 2, various portions of the tubes may be formed or positioned within a plane 26, although during use, as shown in FIGS. 4 and 5, the tubes 4, 6 conform to the face 28 of the user and is self supported on the face and in the mouth 30, meaning the user and/or care giver are not required to hold or position the tubes with their hands, lips, tongue, teeth and/or other devices.

The tubes 4, 6 each have a curved portion 32 forming an ear loop connected to the inlet portion 10. In one embodiment, the ear loop 32 may be encapsulated, or covered with a padding material 40, such as foam, which provides greater comfort to the user. Of course, it should be understood that other portions of the tube, such as the portion 42 running along the face of the user, may also be covered or secured to an interfacing material, such as a padding, to improve comfort.

Another curved portion 34 forms a lip bend. The curved portion 34 is connected to the curved portion 32 with an elongated portion 42 that runs along the face or cheek of the user as shown in FIGS. 4 and 5. As shown in FIGS. 1-3, the curved portion 34 has a curvature that is less than the curvature of the curved portion 32, meaning in this embodiment, the radius of the curved portion 32 is greater than the radius of the second curved portion 34. In one suitable embodiment, the curvature of the curved portion 34 has an inner radius of about 0.25 inches. It should be understood that the curvatures may be other than semi-circular, such as quarter circular, and may for example be curvilinear, or polygonal (i.e., formed from a plurality of discrete linear segments). The term "curvature" refers to the tube having a first portion defining a first vector 44 and a second portion defining a second vector 46, wherein the vectors are co-planar but not the same (meaning they may have different angles or orientations (e.g., parallel but directed in opposite directions)). It should be understood that a curved portion may have multiple curvatures, for example having a curvature in one plane and another curvature in another plane. For example, the curved portion 34, or lip bend, has a plurality of curvatures, including a first curvature in a plane 26 as shown in FIGS. 2 and 3, and a second curvature of a portion thereof as the curved portion 34 transitions to an outlet portion 36 having a curvature in a plane 48 substantially perpendicular to the plane 26. It should be understood that the curvatures may be formed in multiple planes not perpendicular or parallel to each other. In the embodiment of FIGS. 1-3, the curved portions 32, 34 open in opposite first and second directions 50, 52.

The outlet portion 42 extends from the curved portion 32 and terminates in an end portion 38 having a gas exit port 54. The outlet portion 42 has a curvature defined by first and second vectors 44, 46 forming angles β of 30° relative to the plane 26. In one embodiment, the length (L1) of the outlet portion is about 1.6 inches (±2.5 mm, e.g., 1.575 inches), or 1.760 inches (±0.25 mm) from the inner surface of the curved portion 32 to the terminal end of the end portion 38, with the end portion extending below the first plane. The end portion 38 may also be formed as a curved portion, having a curvature in the first plane 26 that may be 0.75 inches and form a vector 56 at an angle α of about 20° with the vertical plane 48 in which the curved portion 36 of the outlet portion lies.

The outlet portion 36, as shown in FIG. 11, is curved such that it extends into the user's mouth 30 and is disposed between the side of a row of upper teeth 58 of the user and the interior surface 60 of the user's cheek. Of course, it should be understood that the configuration and shape can be altered to accommodate placement along the side of the lower teeth or along the occlusal plane. The end portion 38, or curved portion, may be directed laterally inwardly at a targeted region of the rear of the user's mouth 30 and throat. The end portion is configured with the gas exit port 54. In this way, no portion of the tube is disposed between the user's upper and lower teeth. As such, the tube does not interfere with normal speech, eating, drinking swallowing, etc., and does not have to be held in place over or between the user's teeth. In one embodiment, each of the inlet portions, ear loop, lip bend and outlet portion may be integrally formed from a single piece of tubing.

Referring to FIG. 10, an alternative embodiment of an oral cannula includes a manifold 62 that extends across the back of the user's mouth behind the rearmost teeth of the user and connects the tubes 4, 6 on opposite sides of the mouth. The manifold includes one or more gas exit ports 64 formed therein, for example thought a side wall of the manifold, rather through an end portion or lumen. In one embodiment, the manifold may be integrally formed with the other portions of the tubes, such that a single loop of tubing forms and defines the cannula.

Referring to FIGS. 6-9 and 12, another embodiment of an oral cannula for delivering a gas to the mouth of a user includes a housing 70 comprising an inlet portion 72, a riser portion 74 extending upwardly from the inlet portion and a curved outlet portion 76. The housing may be a molded component, formed for example and without limitation, from a flexible material such as silicone or an elastomeric material. The inlet, riser and outlet portions are shaped and configured to conform to, and match the contours of, the user's mouth and lips. The housing is further configured to hold and shape one or more flexible tubes 78, 80, such that the tubing is properly positioned in the user's mouth without interfering with the various oral functions of the user. As such, the housing directs the tubing to the sides of the user's mouth between the outer sides of the user's upper teeth 58 and the interior surface of the cheek 60.

The housing 70 may be made of a single piece, for example with one or two channels that receive the tubing. For example and without limitation, the tubing may be snap-fitted into the channels. In other embodiments, the tubing is threaded through openings formed in the tube. In yet other embodiments, the housing includes first and second housing components. One or more tubes, depending on the application, are disposed between the two housing components, with the housing components being secured to each other, for example and without limitation, by snap fit, welding, mechanical fasteners, adhesives, bonding, or various combinations thereof. The housing may be molded, for example injection molded.

As shown in FIGS. 6-9, the inlet portion 72 may have a pair of channels, with the tubes entering the channels in a first plane, for example and without limitation a horizontal plane 82. The riser portion 74 extends upwardly and rearwardly from the inlet portion. The outlet portion 76 has a pair of branches 84 that extend laterally outwardly and rearwardly from the riser portion. The outlet portion is curved, and has a first curvature when viewing the curved outlet portion from a first direction 86 and a second curvature when viewing the curved outlet portion from a second direction 88, wherein the first and second directions are non-parallel. In one embodiment, the first and second directions are substantially perpendicular. The first curvature 90 matches the curvature of the front teeth of the user and directs the tubes laterally and rearwardly along the teeth. The second curvature 92 forms a dip that provides clearance for the upper labial frenum.

The flexible tubes 78, 80 are coupled to the housing 70 and extend through the inlet portion 72, the riser portion 74 and out of respective ones of the branches 84 of the outlet portion. Each flexible tube has an outlet portion with an end portion extending from the outlet portion 76 of the housing. In one embodiment, the end portion 94 has a curvature that substantially follows and matches the sides of the row of teeth of the user. The end portion has a gas exit port 9 positioned downstream of the outlet portion of said housing. It should be understood that in one embodiment, only a single tube is secured through the housing. In another embodiment, the end portions may be joined by a manifold 62 as shown in FIG. 10.

In any of the embodiments, the oral cannula is configured with orientation indicia 96, which provides information to the user and/or care giver about the orientation and positioning of the cannula. For example and without limitation, in the embodiment of FIGS. 1-5, indicia can be positioned on the adapter 14 and/or slide connector 20 to indicate which surface thereof is the front or back. Likewise, in the embodiment of FIGS. 6-9, indicia can be positioned on the housing 70.

Alternatively, in the embodiment of FIGS. 6-9, the shape of the housing 70 provides a visual indicator, or indicia, about the orientation of the device. In the various embodiments, for example and without limitation, an "R" or "B" can be provided on the back of the connector 20 or other component to indicate "Rear" or "Back," an "F" can be provided to indicate "Front," and/or an "L" or "R" can be provided on the sides, front or back to indicate "Left" and "Right" respectively. Tactile indicia, in the form of Braille characters or raised letters/embossments, can be provided for users and/or care givers with poor sight or for use in poor lighting conditions. Other suitable indicia include without limitation various text (e.g., "Left" and/or "Right"), arrows, various directional indicia and/or combinations thereof. With the use of such indicia, the user and/or care giver can properly locate the oral cannula on the face, and in the mouth, of the user. The adaptor 14 may also be shaped, for example with an angled portion receiving the feed tube 16, so as to direct the feed tube away from the user and provide indicia to the user about the orientation, similar to the shape of the housing 70. Alternatively, a tab, tape or other marker may be provided on the right and left tubes to identify them as such.

In operation, the user or care giver disposes the flexible tube, and in particular the outlet portion 36, between an outer side surface of a row of teeth 58 (upper or lower) and an inner surface 60 of a cheek. In one embodiment, tubes are disposed on opposite sides of the mouth. The tubes are positioned such that the exit ports 54 are positioned in a rear region of the mouth and wherein no portion of the flexible tube is disposed between the upper and lower teeth of the user such that the upper and lower teeth can be closed against each other. In the embodiment of the FIGS. 1-5, the ear loops 32 are disposed around the ears 100 of the user, with the mouth/lip bend being positioned around/over the lip 102 and the outlet portion of the tube being positioned along the side of the teeth as just described. The position of the connector 20 can then be adjusted to further secure the cannula to the user.

In the embodiment of FIGS. 6-9, the housing 70 is inserted between the upper lip 104 and the front 106 of the upper row of teeth, with the tube(s) being positioned along the side of the teeth as described herein. As shown in FIG. 10, either embodiment can be further configured with the manifold 62 extending across the back of the mouth. Alternatively, in either embodiment of FIGS. 1-9, the outlet portion 36, or end portion 38 thereof, may be cut or trimmed such that the exit port 54 is positioned in the proper location in the mouth of the user.

In any of the embodiments, the feed tube 16 is connected to the gas source 22. A gas is then dispensed through the exit port(s) 54, 64, preferably in pulses of predetermine pressure, volume, duration and/or frequency, with the user then swallowing in response to the pulses of gas.

Any of the embodiments of the oral cannula can be made easily, cheaply and quickly without having to make expensive, customized teeth molds. Moreover, the device can be quickly and easily adjusted for a particular user simply by trimming a portion of tubing if necessary. The flexible tube follows the natural contours of the user's face and mouth, yet has sufficient shape memory to ensure proper placement relative to the user's face, lips, mouth and teeth. The flexible tube is self-supporting in the preferred location in the user's mouth, and is maintained in a proper position even with patients/users experiencing numbness or weakness of the lips, tongue or jaw. The device is not fitted over or between the user's upper and lower teeth, and does not have to be held in place by specific jaw positioning. In this way, the flexible tubing, which is disposed between the user's teeth and cheek, does not interfere with normal speech, eating, drinking swallowing, etc., or with the gas pulse delivery and swallowing therapy.

Figure 32:
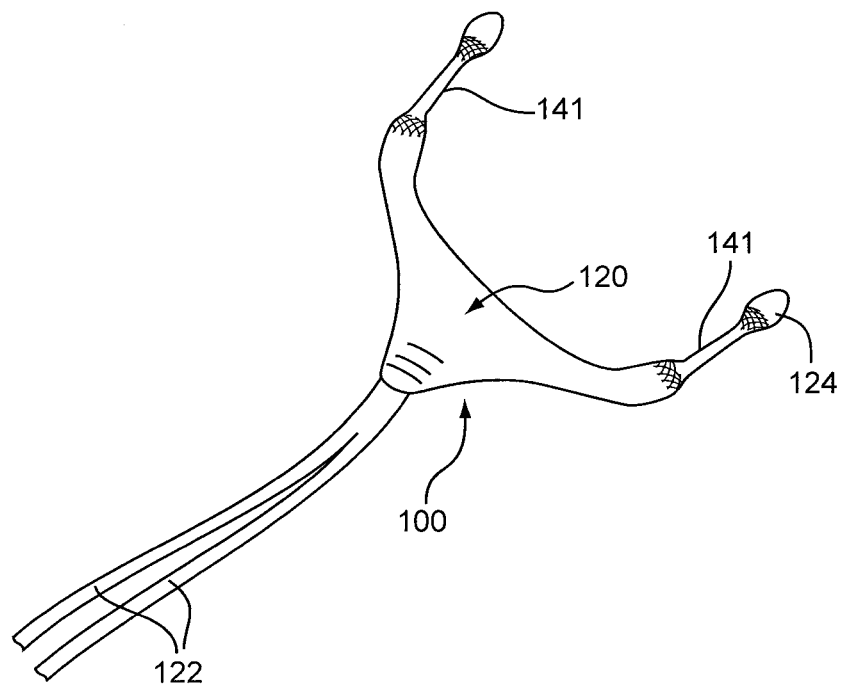
FIG. 32 shows an embodiment of a vibratory SWAPT mouthpiece.

Referring to FIG. 32, in one embodiment, the oral appliance, or part thereof, is made of compliant tubing 141 that absorbs forces applied to its inner surface by the internal pressure of the substance being delivered through the tubing. For example, pressurized gas, delivered through the oral appliance and originating at its input end, will act on the compliant tubing with resulting expansion and contraction of the tubing in direct relation to changes in pressure of the substance within the tubing. In one instance, a gas, controlled by a pressure regulator attached to the input end of the oral appliance, and delivered through the oral appliance, is applied in discrete pressure pulses, such that the region(s) of compliant tubing along the length of the oral appliance expand and contract, for example, within the buccal cavity. Depending upon the frequency of pressure variations of the substance within the oral appliance, and associated expansion and compression of the compliant tubing, a kinetic or vibratory stimulus acts directly upon the surrounding oral tissues, exciting sensory receptors located in the oral mucosal lining.

Figure 33:
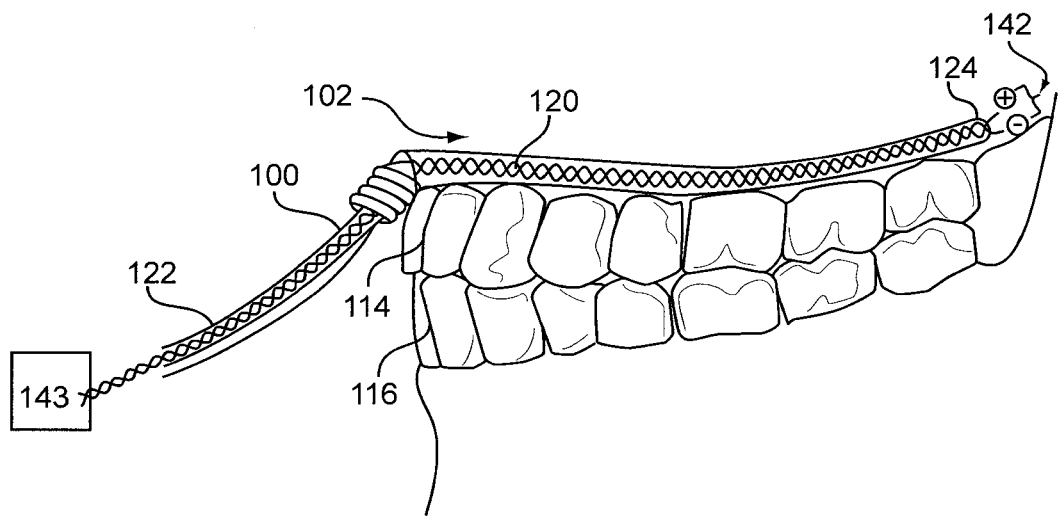
FIG. 33 shows an embodiment of an electrical stimulation SWAPT mouthpiece.

In another embodiment, the substance that is delivered through the oral appliance for the purpose of eliciting a physiological response by the human or animal user may excite sensory receptors of the oral or oropharyngeal regions through a kinetic or a pressure effect. The substance being delivered via the oral appliance can be applied in discrete pulses, for example, air pulses. The air-pulse trains so delivered produce a kinetic effect within the ambient surround of the oral appliance output end, and associated pressures acting upon the oral tissues, exciting sensory receptors. This stimulus may be perceived by the user as vibratory at some stimulus frequencies. In one embodiment shown in FIG. 33, the oral appliance provides a means of positioning a stimulating electrode in the posterior region of the mouth of the human or animal user such that electrical stimulation can be applied to that region. In one embodiment, a bipolar surface skin stimulating electrode 142 is positioned immediately distal to the output end 124 of the oral appliance, and the electrode leads run within the oral appliance tubing within the buccal region of the user 120, continue within the tubing that exits the mouth between the user's lips 122 and exits the tubing to connect to an electrical stimulation control unit 143. With the oral appliance in situ within the buccal region, the stimulating electrode contacts the soft tissues of the rear aspect of the mouth, providing a method for applying electrical stimulation to the oral cavity with the aim of evoking a physiological response in the user, such as a swallowing and/or salivation.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An oral appliance for use with a subject in his/her mouth comprising:
   a mouthpiece comprising an oral body configured to match the curvature of the front teeth of the subject and adapted to be positioned in the subject's oral vestibule, wherein the occlusal surfaces of the subject's teeth are substantially not covered by the mouthpiece, and wherein the mouthpiece comprises a vibratory component, wherein said vibratory component comprises a compliant tube projecting from the oral body and having an inner surface and an exterior surface, wherein said compliant tube is successively expandable and contractable in response to a pressure being applied to said inner surface, wherein said exterior surface is moveable in response to said compliant tube being expanded and contracted, and wherein said exterior surface is adapted to contact and apply a vibratory stimulus to oral tissue in the mouth of the subject.

2. The oral appliance of claim 1 further comprising a pressure source communicating with said compliant tube, wherein said pressure source applies said pressure to said inner surface of said compliant tube.

3. The oral appliance of claim 2 wherein said pressure source comprises a pressurized gas, and further comprising a regulator operable to deliver said pressurized gas in pressure pulses, wherein said compliant tube is successively expandable and contractable in response to said pressure pulses.

4. The oral appliance of claim 1 wherein said vibratory component comprises a pair of said compliant tubes.

5. The oral appliance of claim 4 wherein said mouthpiece comprises a housing having an inlet portion and a pair of spaced apart outlet portions extending laterally outwardly from said inlet portion, each of said outlet portions supporting one of said compliant tubes.

6. The oral appliance of claim 5 wherein said compliant tubes extend from said inlet portion in a side-by-side relationship.

7. The oral mouthpiece of claim 1 wherein said oral mouthpiece is coated with an oral disinfectant.

8. The oral appliance of claim 1 wherein said compliant tube is free of any through holes between said interior and exterior surfaces.

9. The oral appliance of claim 1 wherein said compliant tube comprises an end portion having a fluid output port.

10. A method of stimulating a region of a user's oral cavity comprising:
    positioning a vibratory component of a mouthpiece comprising an oral body configured to match the curvature of the front teeth of the user, in the user's oral vestibule, wherein the occlusal surfaces of the user's teeth are not covered by the mouthpiece, wherein said vibratory component comprises a compliant tube projecting from the oral body and having an inner surface and an exterior surface;

applying a pressure to an inner surface of said compliant tube and expanding said compliant tube; and applying a vibratory stimulus to an oral tissue of the user with said exterior surface of said compliant tube.

11. The method of claim 10 wherein said applying said pressure to said inner surface comprises supplying said compliant tube with a pressurized gas from a pressure source.

12. The method of claim 11 wherein said supplying said compliant tube with said pressurized gas comprises delivering said pressurized gas in pressure pulses with a regulator, and wherein said expanding said compliant tube comprises expanding and contracting said compliant tube in response to said pressure pulses.

13. The method of claim 10 wherein said vibratory component comprises a pair of said compliant tubes, wherein said applying said pressure to said inner surface of said compliant tube comprises applying said pressure to said inner surface of each of said pair of compliant tubes and expanding each of said pair of said compliant tubes.

14. The method of claim 13 wherein said mouthpiece comprises a housing having an inlet portion and a pair of spaced apart outlet portions extending laterally outwardly from said inlet portion, each of said outlet portions supporting one of said pair of compliant tubes.

15. The method of claim 14 wherein said pair of said compliant tubes extends from said inlet portion in a side-by-side relationship.

16. The method of claim 10 wherein said oral mouthpiece is coated with an oral disinfectant.

17. The method of claim 10 wherein said compliant tube is free of any through holes between said interior and exterior surfaces.

18. The method of claim 10 further comprising dispensing a substance through an output port defined by an end portion of said compliant tube.

* * * * *